US008563699B2

(12) United States Patent
Bogoch et al.

(10) Patent No.: US 8,563,699 B2
(45) Date of Patent: Oct. 22, 2013

(54) ANTHRAX AND SMALL POX REPLIKINS AND METHODS OF USE

(76) Inventors: Samuel Bogoch, New York, NY (US); Elenore S. Bogoch, New York, NY (US)

( * ) Notice: Subject to any disclaimer, the term of this patent is extended or adjusted under 35 U.S.C. 154(b) by 199 days.

(21) Appl. No.: 12/688,372

(22) Filed: Jan. 15, 2010

(65) Prior Publication Data

US 2011/0171236 A1 Jul. 14, 2011

Related U.S. Application Data

(60) Division of application No. 11/615,578, filed on Dec. 22, 2006, now Pat. No. 7,674,880, which is a continuation of application No. 09/984,056, filed on Oct. 26, 2001, now Pat. No. 7,176,275.

(60) Provisional application No. 60/303,396, filed on Jul. 9, 2001, provisional application No. 60/278,761, filed on Mar. 27, 2001.

(51) Int. Cl.
*C07K 16/12* (2006.01)
*A61K 39/40* (2006.01)

(52) U.S. Cl.
USPC .................. 530/388.4; 530/387.9; 424/139.1; 424/164.1

(58) Field of Classification Search
None
See application file for complete search history.

(56) References Cited

U.S. PATENT DOCUMENTS

| | | | |
|---|---|---|---|
| 4,132,769 A | 1/1979 | Osther | |
| 5,104,854 A | 4/1992 | Schlesinger et al. | |
| 5,231,167 A | 7/1993 | Zanetti et al. | |
| 5,280,113 A | 1/1994 | Rademacher | |
| 5,580,767 A | 12/1996 | Cowsert | |
| 5,679,352 A | 10/1997 | Chong | |
| 5,866,690 A | 2/1999 | Bogoch | |
| 6,023,659 A | 2/2000 | Seilhamer | |
| 6,070,126 A | 5/2000 | Kokolus | |
| 6,090,406 A | 7/2000 | Popescu | |
| 6,242,578 B1 | 6/2001 | Bogoch et al. | |
| 6,256,647 B1 | 7/2001 | Toh | |
| 6,470,277 B1 | 10/2002 | Chin | |
| 6,484,166 B1 | 11/2002 | Maynard | |
| 6,638,505 B2 | 10/2003 | Bogoch | |
| 7,176,275 B2 | 2/2007 | Bogoch | |
| 7,189,800 B2 | 3/2007 | Bogoch | |
| 7,420,028 B2 | 9/2008 | Bogoch | |
| 7,442,761 B2 | 10/2008 | Bogoch | |
| 7,452,963 B2 | 11/2008 | Bogoch | |
| 7,674,880 B2 | 3/2010 | Bogoch et al. | |
| 7,705,129 B2 | 4/2010 | Bogoch | |
| 7,758,863 B2 | 7/2010 | Bogoch | |
| 7,763,705 B2 | 7/2010 | Bogoch | |
| 7,774,144 B2 | 8/2010 | Bogoch | |
| 7,894,999 B2 | 2/2011 | Bogoch | |
| 8,050,871 B2 | 11/2011 | Bogoch | |
| 2005/0271676 A1 | 12/2005 | Sette et al. | |

FOREIGN PATENT DOCUMENTS

| | | |
|---|---|---|
| DE | 3628658 | 3/1988 |
| DE | 3628658 A1 | 3/1988 |
| EP | 0 108 564 A1 | 5/1984 |
| IT | 98MI0874 | 10/1999 |
| JP | 9121867 | 5/1997 |
| JP | 11001493 | 1/1999 |
| KR | 10-1999-0008052 | 1/1999 |
| WO | 96/32106 | 10/1996 |
| WO | 96/36436 | 11/1996 |
| WO | 0018351 A | 4/2000 |
| WO | 00/52054 | 9/2000 |
| WO | 200104135 A2 | 1/2001 |

OTHER PUBLICATIONS

Uniprot Sequence Database comparison sheet Mar. 22, 2011.*
hypothetical protein pxo1_107 sequence printout, printed Nov. 3, 2011.*
ACML01000595 database entry dated Oct. 30, 2011.*
SG Written Opinion, Application No. SG 200602419-4, Aug. 3, 2010.
US Office Action, U.S. Appl. No. 12/495,306, Sep. 1, 2010.
PCT International Search Report, PCT/US2002/09240, Jan. 14, 2004, USPTO, International Searching Authority, Washington DC.
PCT International Preliminary Examination Report, PCT/US2002/09240, Feb. 5, 2004, USPTO, International Preliminary Examination Authority, Alexandria, VA, USA.
PCT International Search Report, PCT/US2002/21494, May 30, 2003, USPTO, International Searching Authority, Washington DC.
PCT International Preliminary Examination Report, PCT/US2002/21494, Nov. 26, 2004, USPTO, International Searching Authority, Alexandria, VA, USA.
PCT International Search Report, PCT/US2003/08990, Dec. 7, 2005, International Searching Authority, USPTO, Alexandria, VA, USA.
PCT Written Opinion of the International Searching Authority, PCT/US2004/017936, Apr. 7, 2005, EPO, International Searching Authority, Munich, DE.
PCT International Search Report, PCT/US2004/017936, Apr. 28, 2005, EPO, International Searching Authority, Rijswijk, NL.
PCT International Preliminary Report on Patentability, PCT/US2004/017936, Apr. 13, 2007, USPTO, International Preliminary Examining Authority, Alexandria, VA, USA.

(Continued)

*Primary Examiner* — Mary E Mosher
*Assistant Examiner* — Myron Hill
(74) *Attorney, Agent, or Firm* — Daren P. Nicholson

(57) ABSTRACT

Isolated peptides of the *Bacillus anthracis* Anthrax Toxin Lethal factor Protein pX01-107, antibodies specific for the peptides and methods of stimulating the immune response of a subject to produce antibodies to the *Bacillus anthracis* Anthrax Toxin Lethal factor Protein pX01-107 are disclosed. Also disclosed are isolated peptides of the Small Pox Virus Surface Antigen S Precursor Protein, antibodies specific for the peptides and methods of stimulating the immune response of a subject to produce antibodies to the Small Pox Virus Surface Antigen S Precursor Protein.

19 Claims, 7 Drawing Sheets

(56) References Cited

OTHER PUBLICATIONS

PCT International Search Report, PCT/US2005/014443, Oct. 21, 2005, EPO, International Searching Authority, Rijswijk, NL.
PCT Written Opinion of the International Searching Authority, PCT/US2005/014443, Apr. 12, 2006, EPO, International Searching Authority, Munich, DE.
PCT International Preliminary Report on Patentability, PCT/US2005/014443, Nov. 1, 2006, WIPO, International Bureau of WIPO, Geneva, Switzerland.
PCT International Search Report, PCT/US2006/05343, Sep. 25, 2007, USPTO, International Searching Authority, Alexandria, VA, USA.
Supplementary Partial European Search Report 99944002, Apr. 20, 2004, EPO, Munich, DE.
Supplementary Partial European Search Report 02736514.7, Mar. 9, 2006.
Supplementary Partial European Search Report 02752202.8, Mar. 10, 2006.
Supplementary Partial European Search Report 03721445.9, Dec. 12, 2006 , EPO, International Searching Authority, Munich, DE.
NCBI accession # gi 75059 Jul. 16, 1999.
NCBI Accession # AAK38298, Apr. 19, 2001.
NCBI Accession No. Np 740460, Dec. 3, 2003.
NCBI Blast Searching, Gene Gateway—Exploring Genes and Genetic Disorders, "Sequence similarity searching using NCBI Blast" (http:www.ORNL.gov/sci/techresources/Himan_Genome/chromosome/blast.shtml), Apr. 27, 2005.
NCBI Query Tutorial "Introduction" (http://www.ncbi.nim.nih.gov/Education/BLASTinfo/query_tutorial.html), Apr. 27, 2005.
NCBI Query Tutorial "Introduction to a BLAST Query" (http://www.ncbi.nim.nih.gov/Education/BLASTinfo/tut1.html), Apr. 27, 2005.
NCBI Query Tutorial "Setting up a BLAST Search" (http://www.ncbi.nim.nih.gov/Education/BLASTinfo/Blast_setup.html), Apr. 27, 2005.
3MOTIF—Search Instructions, 3motif in three Dimensions, article titles "Submitting a protein sequence": http://brutlag.stanford.edu/3motif/search_instr.html), Apr. 27, 2005.
Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.
Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.
Bogoch et al., "Aglyco Pathology of Viral Receptors in Dementias," Annals of the New York Academy of Sciences, New York Academy of Sciences, New York Academy of Sciences, New York, NY, US, vol. 757, 1995, pp. 413-417, XP008003395, ISSN:0077-8923.
Brumeanu, T.M. et al., "Immunogenicity of a Contiguous T-B Synthetic Epitope of the A/PR/8/34 Influenza Virus," Journal of Virology, Jul. 1997, vol. 71, No. 7, pp. 5473-5480.
Bucher, D. et al., "M protein (M1) of influenza virus antigenic analysis and intracellular localization with monoclonal antibodies", J Virol. Sep. 1989; 63(9): pp. 3622-3633.
Yasuko, A-0, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct. 2006.
Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).
Gelder, C.M. et al., "Human CD4+ T-cell repertoire of response to influnza A virus hemagglutinin after recent natural infection," Journal of Virology, Dec. 1995, vol. 69, No. 12, pp. 7497-7506A.
Keppeler et al., "Elongation of thr N-acyl side chain of sialic acid in MDCK II cells inhibits influenza A virus infection," abstract, Biochemical and Biophysical Research Communications, Dec. 18, 1998,
vol. 253, No. 2. Database Medline on STN, National Library of Medicine, (Bethesda, MD, USA), No. 99097253.
Kornblith P. L. et al., "Growth-inhibitory effect of diphenylhydantoin on murine astrocytomas," Neurosurgery, vol. 5, No. 2, pp. 259-263 (Aug. 1979), MEDLINE, XP002199627.
Margalit et al., "Prediction of Immunodominant Helper T Cell Antigenic Sites From the Primary Sequence," Jour. of Immunology, vol. 138, 2213-2229, Apr. 1, 1987.
Seal et al., "Elevation of Serum Protein-Bound Carbohydrates and Haptoglobin in Schizophrenia," Clinical Chemistry; Oct. 1996, vol. 12, No. 10, pp. 709-716.
Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.
Weber, E. et al., "Fine Mapping of a Peptide Sequence Containing an Antigenic Site Conserved Among Arenaviruses," Virology, vol. 164, p. 30-38 (1988).
Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc., ISSN: 0090-0877.
Ben-Yedidia, T. et al., "Intranasal administration of peptide vaccine protects human/mouse radiation chimera from influenza infection," International Immunology, 1999, pp. 1043-1051, ISSN: 0953-8178.
Betakova, et al., "The Vaccinia Virus A14.5L Gene Encodes a Hydrophobic 53-Amino-Acid Virion Membrane Protein That Enhances Virulence in Mice and Is Conserved among Vertebrate Poxviruses," Journal of Virology, vol. 74., No. 9, May 2000, p. 4085-4092.
Bogoch et al., "In vitro production of the general transformation antibody related to survival in human cancer patients; antimalignin antibody," Abstract, Cancer Detection and Prevention, 1988, vol. 12, Nos. 1-6, pp. 313-320 (Database Medline on STN, National Library of Medicine, (Bethesda, MD, USA), No. 89028479).
Brown, L. R. et al., "Recognition of the influenza hemagglutinin by Class II MHC-restricted T lymphocytes and antibodies," Journal of Immunology, Oct. 15, 1991, pp. 2677-2684, vol. 147, No. 8, American Association of Immunologists, USA, ISSN: 0022-1767.
Carr, C. M. et al., "A spring-loaded mechanism for the conformational change of influenza hemagglutinin," Cell, May 21, 1993, pp. 823-832, vol. 73, Cell Press, ISSN: 0092-8674.
Gao, Xiao-Ming, et al., "Identification and Characterization of T Helper Epitopes in the Nucleoprotein of Influenza A Virus," The Journal of Immunology, vol. 143, No. 9, pp. 3007-3014, (Nov. 1999).
Massung et al., "Potential virulence determinants in terminal regions of variola spallpox virus genome," Nature, vol. 366, Dec. 23-30, 1993, p. 748-751.
Orlando, C. et al., "A monoclonal antibody directed against the catalytic site of Bacillus anthracis adenylyl cyclase identifies a novel mammalian brain catalytic subunit," Biochemistry, 1992, pp. 3215-3222, vol. 31, American Chemical Society, ISSN: 0006-2960.
Pannifer, Andrew D., et al. "Crystal structure of the anthrax lethal factor," Nature , vol. 414, p. 229-233, (Nov. 2001).
Patil et al., "Identification of a Talin-binding Site in the Integrin β3 Subunit Distinct from the NPLY Regulatory Motif of a Post-ligand Binding Functions," The Journal of Biological Chemistry, vol. 274, No. 1, Oct. 1, 1999, p. 28575-28583.
Rodman, Toby C., et al., "Human Immunodeficiency Virus (HIV) Tat-reactive Antibodies Present in Normal HIV-negative Sera and Depleted in HIV-positive Sera. Identification of the Epitope," vol. 175, pp. 1247-1253, (May 1992).
Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.
US Office Action, U.S. Appl. No. 11/615,578, Oct. 21, 2009.
Schenk, S. et al., "Four recombinant isoforms of Cor a 1, the major allergen of hazel pollen, show different reactivities with allergen-specific T-lymphocyte clones," European Journal of Biochemistry, 1994, pp. 717-722, vol. 224, ISSN: 0014-2956.

(56) References Cited

OTHER PUBLICATIONS

Sharma et al., "Synthesis and Characterization of a Peptide Identified as a Functional element in αA-crystallin," The Journal of Biological Chemistry, vol. 275, No. 6, Feb. 11, 2000, p. 3767-3771.
Shi, Ya Ping, et al., "Immunogenicity and in vitro protective efficacy of a recombinant multistage Plasmodium falciparum candidate vaccine," Proc. Natl. Acad. Sci., vol. 96, pp. 1615-1620, (Feb. 1999).
Ping Zhao, et al. "Neutralizing monoclonal antibody against Anthrax lethal factor inhibits intoxication in a mouse model," Human Antibodies, vol. 12, p. 129-135, (2003).
EP Office Action 04785929.3, Sep. 1, 2008, EPO, Netherlands.
EP Office Action 04785929.3, Feb. 2, 2009, EPO, Netherlands.
NCBI listing JQ0032 (May 11, 2000)—residues 74-82.
NCBI Swiss-Prot Locus P33795, accessed Jul. 20, 2009.
NZ Office Action 553983, Jul. 16, 2008, IPO, New Zealand.
NZ Office Action 560415, Mar. 6, 2009, IPO, New Zealand.
PCT International Search Report and Written Opinion, PCT/US2007/069978, Jun. 3, 2008, EPO, International Searching Authority, Rijswijk, NL.
PCT International Search Report and Written Opinion, PCT/US2007/82436, Jan. 9, 2009, USPTO, International Searching Authority, Alexandria, VA, USA.
PCT International Search Report and Written Opinion, PCT/US2008/00645, Feb. 2, 2009, USPTO, International Searching Authority, Alexandria, VA, USA.
PCT International Search Report and Written Opinion, PCT/US2008/061336, Feb. 2, 2009, EPO, International Searching Authority, Rijswijk, NL.
PCT International Preliminary Report on Patentability, PCT/US2007/069978, May 1, 2009, USPTO, International Preliminary Examining Authority, Alexandria, VA, USA.
PCT International Preliminary Report on Patentability, PCT/US2006/05343, Jul. 22, 2008, USPTO, International Preliminary Examining Authority, Alexandria, VA, USA.
PepBank entry 42800, corresponding to UniProt database entry P15516, Apr. 1, 1990 (Homo sapiens salival protein histatin), available at http://pepbank.mgh.harvard.edu, accessed Oct. 6, 2008.
UnitProt/Swiss-Prot database entry O89746 1 Influenza A virus (strain A/Chicken/Hong Kong/220/1997 H5N1 genotype Gs/Gd) dated Nov. 1, 1998.
EP Supplemental Search, EP 10 01 2945.1, Jun. 9, 2011, EPO, Munich, DE.
CA Office Action, CA 2,441,540, Jul. 11, 2011, CIPO, CA.
CN Office Action, CN 200580012974.0, Jul. 19, 2011, CIPO, CN.
EP Partial Search Report, EP 11 158 084.1, Oct. 7, 2011, EPO.
EP Partial Search Report, EP 11 158 093.2, Oct. 14, 2011, EPO.
KR Office Action, KR 2006-7021152, Dec. 8, 2011, KIPO.
Buscaglia et al., "The repetitive domain of Trypanosoma cruzi trans-sialidase enhances the immune response against the catalytic domain," Journal of Infectious Diseases, University of Chicago Press, Chicago, IL, vol. 177, No. 2, Feb. 1, 1998, pp. 431-436.
Cross et al., "Studies on influenza haemagglutinin fusion peptide mutants generated by reverse genetics," The EMBO Journal vol. 20 No. 16 pp. 4432-4442, 2001.
Ferro et al., "The androgen receptor CAG repeat: a modifier of carcinogenesis?" Molecular and Cellular Endocrinology, 193, Jan. 1, 2002, pp. 109-120.
Melville et al., "P58IPK, a novel cochaperone containing tetratricopeptide repeats and a J-domain with oncogenic potential," Database accession No. PREV200000253165; & CMLS Cellular and Molecular Life Sciences, vol. 57, No. 2, Feb. 2000, pp. 311-322, ISSN: 1420-682X.
Okuno et al., "A Common Neutralizing Epitope Conserved between the Hemagglutinins of Influenza A Virus H1 and H2 Strains," Journal of Virology, vol. 67, No. 5, May 1993, p. 2552-2558.
Simeckova-Rosenberg et al., "Protection of mice against lethal viral infection by synthetic peptides corresponding to B- and T-cell recognition sites of influenza A hemagglutinin," VACCINE, vol. 13, No. 10, pp. 927-932 (1995).
Smith et al., "Finding sequence motifs in groups of functionally related proteins," PNAS, vol. 87, pp. 826-830, Jan. 1990.
Sg Written Opinion, Application No. Sg 200602419-4, 2010-08-03.
US Office Action, Application No. 12/495,306, 2010-09-01.
US Office Action, Application No. 12/170,763, 2011-02-15.
US Office Action, Application No. 12/252,028, 2011-02-15.
US Office Action, Application No. 12/495,306, 2011-02-15.
US Office Action, Application No. 12/010,027, 2011-02-16.
US Office Action, Application No. 12/696,712, 2011-03-28.
SG Written Opinion, Application No. SG 200602420-2, Apr. 6, 2011.
US Office Action, U.S. Appl. No. 121789,877, Jun. 8, 2011.
Diggs et al., Experimental Parasitology, vol. 80, Issue 2, Mar. 1995, pp. 291-296.
Frankel, et al., PNAS 1989, vol. 86, pp. 7397-7401.
Fern, J. "Promiscuous malaria peptide epitope stimulates CD45Ra T cells from peripheral blood of nonexposed donors," J. Immunology 1992, vol. 148, pp. 907-913.
He, Z. et al., "Identification of epitopes in cucumber mosaic virus using a phage-displayed random peptide library," J Gen Virol 1998, vol. 79, pp. 3145-3153.
Helgason et al. (2000), Appl Environ Microbiol 66: 2627-2630.
Hoffmaster et al., "Identification of anthrax toxin genes in a *Bacillus cereus* associated with an illness resembling inhalation anthrax,": PNAS, Jun. 1, 2004, vol. 101, No. 22, pp. 8449-8454.
Klee et al., "The Genome of a Bacillus Isolate Causing Anthrax in Chimpanzees Combines Chromosomal Properties of B. cereus with B. anthracis Virulence Plasmids," PLoS One, Jul. 2010, vol. 5, Issue 7, e10986, pp. 1-12.
Patarroyo et al., Nature, vol. 328, No. 6131, Aug. 13, 1987, pp. 629-632.
Rasko et al., "Complete Sequence Analysis of Novel Plasmids from Emetic and Periodontal Bacillus cereus Isolates Reveals a Common Evolutionary History among the B. cereus-Group Plasmids, Including Bacillus anthracis pXO1," Journal of Bacteriology, Jan. 2007, vol. 189, No. 1, p. 52-64.
Rodriguez et al., "Plasmodium falciparum EBA-175 kDa protein peptides which bind to human red blood cells." Parasitology (2000), vol. 120, pp. 225-235.
Takahashi, et al., Clinical cancer research 1995, vol. 1, pp. 1071-1077.
Yao et al., Int J Peptide Protein Res 1996 vol. 5, pp. 477-485.
NCBI Accession No. YP_003786975, Jul. 21, 2010.
NCBI Accession No. YP_002267796, Oct. 6, 2008.
EP Supplemental Search EP 10 01 2944, Apr. 20, 2011, EPO, Munich, DE.
Kumar, et al., "Cytotoxic T Cells Specific for the Circumsporozoite Protein of Plasmodium Falciparum," Nature, vol. 334, Jul. 21, 1988, pp. 258-260, XP002027064.
Lal et al., "Identification of T-cell determinants in natural immune responses to the Plasmodium falciparum apical membrane antigen (AMA-1) in an adult population exposed to malaria," Infection and Immunity, vol. 64, No. 3, Mar. 1996, pp. 1054-1059, XP055000060.
Ostroff, "Emerging infectious diseases 1997-1998: The role of molecular epidemiology," Memorias Do Instituto Oswaldo Cruz, vol. 94, No. 1, Jan. 1999, pp. 1-3, XP002636692.

* cited by examiner

ANTHRAX AND SMALL POX REPLIKINS AND METHODS OF USE

CROSS REFERENCE TO OTHER APPLICATIONS

This application is a divisional application of U.S. application Ser. No. 11/615,578, filed Dec. 22, 2006, now U.S. Pat. No. 7,674,880, which is a continuation of U.S. application Ser. No. 09/984,056, filed Oct. 26, 2001, now U.S. Pat. No. 7,176,275, and claims priority to Provisional Application Ser. Nos. 60/303,396 filed Jul. 9, 2001 and 60/278,761 filed Mar. 27, 2001, which are incorporated herein in their entirety by reference thereto.

SEQUENCE LISTING

The instant application contains a Sequence Listing, which has been submitted in ASCII format via EFS-Web and is hereby incorporated by reference in its entirety. Said ASCII copy, created on Jan. 28, 2013, is named 13794469.txt and is 17,434 bytes in size.

FIELD OF THE INVENTION

This invention relates to the identification and use of Replikins, a class of peptides that share structural characteristics. In particular, this invention relates to Replikins which have been identified in *Bacillus anthracis* and Small Pox Virus (Variola).

BACKGROUND OF THE INVENTION

Glycoprotein 10B is a membrane glycoprotein isolated from brain glioblastoma multiforme, lymphoma and breast cancer cells (U.S. Pat. No. 6,242,578 B1). A constituent peptide of Aglyco 1OB, malignin, is enriched in cell membranes tenfold during anaerobic replication. Hydrolysis and mass spectrometry of malignin yielded a 16-mer peptide including (SEQ ID NO.: 1) kagvaflhkk. This peptide, which is absent from the normal human genome, was assumed to be acquired.

SUMMARY OF THE INVENTION

In one aspect of the invention there are provided isolated *Bacillus anthracis* (Anthrax) peptides containing a replikin sequence. The Anthrax peptides comprise from 7 to about 50 amino acids including (1) at least one lysine residue located six to ten amino acid residues from a second lysine residue; (2) at least one histidine residue; and (3) at least 6% lysine residues. In another embodiment of this aspect of the invention there are provided Small Pox Virus peptides containing a replikin sequence which comprises from 7 to about 50 amino acids including (1) at least one lysine residue located six to ten amino acid residues from a second lysine residue; (2) at least one histidine residue; and (3) at least 6% lysine residues.

In another aspect of the invention there is provided a process for stimulating the immune system of a subject to produce antibodies that bind specifically to Anthrax polypeptides containing a replikin sequence, said process comprising administering to the subject an effective amount of a dosage of a composition comprising at least one Anthrax replikin peptide. In a preferred embodiment the composition comprises at least one peptide selected from SEQ ID NO. 91, SEQ ID NO. 92, SEQ ID NO. 93, SEQ ID NO. 94, SEQ ID NO. 95, SEQ ID NO. 96, SEQ ID NO. 79, SEQ ID NO. 98 or a combination thereof.

In another embodiment of this aspect of the invention there is provided a process for stimulating the immune system of a subject to produce antibodies that bind specifically to Small Pox Virus polypeptides containing a replikin sequence, said process comprising administering to the subject an effective amount of a dosage of a composition comprising at least one Small Pox Virus replikin peptide. In a preferred embodiment the composition comprises a peptide selected from SEQ ID NO. 99, SEQ ID NO. 100, SEQ ID NO. 101, SEQ ID NO. 102, SEQ ID NO. 103, or a combination thereof.

In another aspect of the invention there are provided antisense nucleic acid molecules complementary to the coding strand of the gene or to the mRNA encoding the *Bacillus anthracis* Anthrax Lethal Factor Protein pX01-107 peptide, wherein said antisense nucleic acid molecule is complementary to a nucleotide sequence encoding the peptide of SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98.

There are also provided antisense nucleic acid molecule complementary to the coding strand of the gene or to the mRNA encoding the Small Pox Virus Surface Antigen S Precursor Protein, wherein said antisense nucleic acid molecule is complementary to a nucleotide sequence encoding the peptide of SEQ ID NO. 99, SEQ ID NO. 100, SEQ ID NO. 101, SEQ ID NO. 102, or SEQ ID NO. 103.

As used herein, the term "peptide" refers to a compound of two or more amino acids in which the carboxyl group of one is united with an amino group of another, forming a peptide bond. The term peptide is also used to denote the amino acid sequence encoding such a compound. Thus, a peptide sequence may be a subsequence of a larger polypeptide sequence. As used herein, a Replikin peptide is peptide consisting essentially of 7 to about 50 amino acid including (1) at least one lysine residue located six to ten amino acid residues from a second lysine residue; (2) at least one histidine residue; and (3) at least 6% lysine residues. Similarly, a replikin sequence is the amino acid sequence encoding such a peptide.

DETAILED DESCRIPTION OF THE INVENTION

Figure 1:
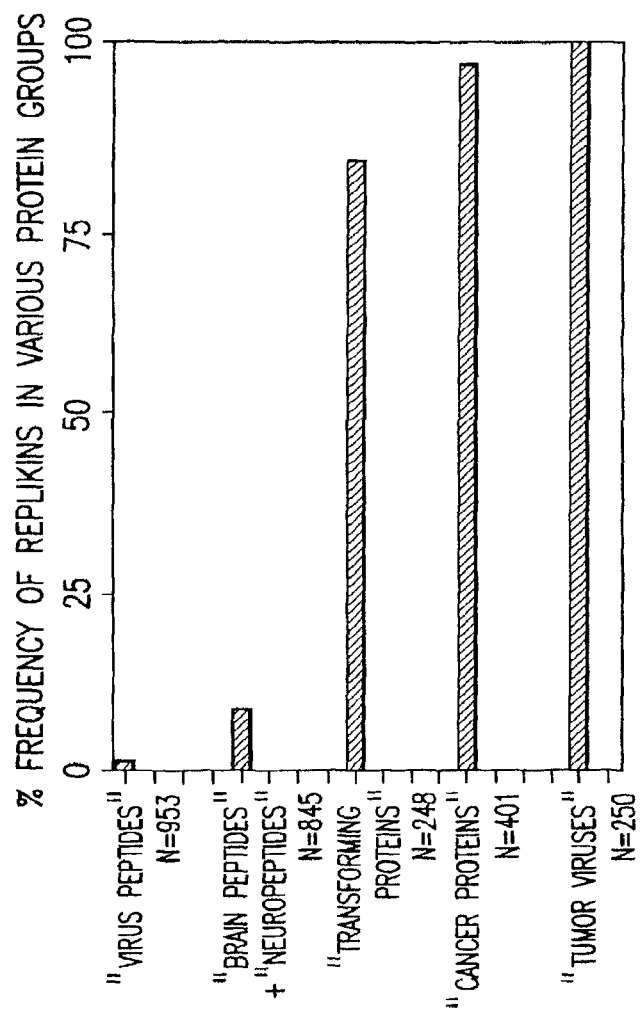
FIG. 1 is a bar graph depicting the frequency of occurrence of replikins in various protein groups.

In one aspect of the invention there is provided a method for identifying nucleotide or amino acid sequences that include a recognin or replikin sequence. The method is referred to herein as a 3-point-recognition method. By use of the "3-point recognition" method, described herein below, a new class of peptides was revealed in algae, yeast, fungi, amoebae, bacteria, plant and virus proteins having replication, transformation, or redox functions. This class of peptides is referred to herein as replikins.

One example of a replikin that was identified by the 3-point-recognition method, is the amino acid sequence, (SEQ ID NO.: 2) hsikrelgiifdk, which occurs in *Saccharomyces cerevisiae* "replication binding protein". Five replikins were found in amino acids 1-163 of the "replicating protein" of tomato leaf curl *Gemini vinis*. Amino acids 1-160 of this tomato virus protein bind DNA. Another replikin, (SEQ ID NO.: 3) hkqkivapvk, is highly conserved in 236 isolates of foot and mouth disease virus.

Although replikins were found to be present in only 1.5% of published sequences identified by the PubMed data bank as "virus peptides" as a whole, and in only 8.5% of sequences identified as "brain peptides" plus "neuropeptides", surprisingly, replikins were found in 100% of "tumor viruses", in 85% of "transforming proteins," and 97% of "cancer proteins" (as categorized in the PubMed data bank). The recognin, (SEQ ID NO.: 4) ykagvaflhkkndide, was not found in published sequences of the human genome.

The 16-mer recognin peptide, (SEQ ID NO.: 4) ykagvaflhkkndide, when synthesized and injected as vaccine into a mammal, has been shown to produce antimalignin antibody, which is cytotoxic to malignant replicating cells of several types at picogram per cell amounts. Replikins identified in organisms such as diatom plankton, *H. pylori*, tomato leaf curl virus, foot and mouth disease virus, hepatitis B and C viruses, and HIV, also are thus targets for diagnosis and treatment or as vaccines for the control of replication of their respective virus source.

Table 1 illustrates the sequence of the malignin peptide, the 16-mer recognin sequence, (SEQ ID NO.: 4) ykagvaflhkkndide.

TABLE 1

| | | | 16-mer peptide sequence ykagvaflhkkndide obtained from malignin by hydrolysis and mass spectrometry | | | |
|---|---|---|---|---|---|---|
| | | | | Method By Which Fragment Obtained | | |
| Seq ID NO. | Fragment Identified | MH+ (mass) | Sequence | Auto-hydrolysis of malignin free in solution | Auto-hydrolysis of malignin immobilized on bromoacetyl cellulose | Microwaved 5 seconds | Microwaved 30 seconds |
| 19 | 1-3 | 381.21 | ( )yka(g) | | | | + |
| 20 | 1-5 | 537.30 | ( )ykagv(a) | | + | | |
| 21 | 2-6 | 445.28 | (y)kagva(f) | | + | | |
| 22 | 2-7 | 592.35 | (Y)kagvaf(l) | | | + | |
| 23 | 4-11 | 899.55 | (a)gvaflhkk(n) | | | | + |
| 24 | 5-7 | 336.19 | (g)vaf(l) | | | | + |
| 25 | 6-7 | 237.12 | (v)af(l) | + | | | |
| 26 | 6-10 | 615.36 | (v)aflhk(k) | | | | + |
| 27 | 6-10 | 615.36 | (v)aflhk(k) | + | | | |
| 28 | 6-12 | 857.50 | (v)aflhkkn(d) | | + | | |
| 29 | 6-12 | 857.50 | (v)afhkkn(d) | + | | | |
| 30 | 7-8 | 279.17 | (a)fl(h) | | | + | |
| 31 | 10-16 | 861.43 | (h)kkndide( ) | | + | | |
| 32 | 11-14 | 489.27 | (k)kndi(d) | | + | | |
| 33 | 12-15 | 476.2- | (k)ndid(e) | + | | | |

The malignin peptide was isolated from membranes of glioblastoma multiforme (glioma) cells grown in tissue culture (U.S. Pat. No. 6,242,578 B1). The sequence of a 16-mer peptide of malignin was determined by hydrolysis and mass spectrometry: (SEQ ID NO.: 4) ykagvaflhkkndide (Table 1). A search of published human genome sequences for sequence encoding the 16-mer amino acid sequence was negative. Since this 16-mer peptide was absent from normal human genome data a search was made of sequences of other organisms for possible origins and homologues. No identical sequences were found. But, using the sequence of the 16-mer peptide as a template, and constructing a "3-point-recognition" method to visually scan protein sequences of several different organisms, a new class of peptides, the replikins, was revealed in organisms as diverse as algae, yeast and viruses. Surprisingly, these peptides were found to be concentrated in larger 'replicating' and 'transforming' proteins (so designated by their investigators, based on activities, see Table 2).

Table 2 illustrates several replikin sequences that were identified by the 3-point-recognition method of the invention.

TABLE 2

Examples of replikins in various organisms - prototype: Glioma replikin* kagvaflhkk
(SEQ ID No.: 1)

| | SEQ ID NO. | | | |
|---|---|---|---|---|
| Algae: | | 34 | *Caldophera prolifera* | kaskftkh |
| | | 35 | *Isolcpisprolifera* | kaqaetgeikgh |
| Yeast: | | 36 | *Schizosaccharomyces pombe* | ksfkypkkhk |
| | | 2 | *Sacch. cerevisiae* replication binding protein | hsikrelgiifdk |
| Fungi: | | 38 | Isocitrate lyase ICl 1, *Penicillium marneffei* | kvdivthqk |
| | | 39 | NA-dependent RNA polymerase 11, *Diseula destructiva* | kleedaayhrkk |
| | | 40 | *Ophiostoma novo*-u1m 1, RNA in Dutch elm disease fungus | kvilplrgnikgiffkh |
| Amoeba: | | 41 | *Entamoeba invadens*, histone H2B | klilkgdlnkh |
| Bacteria: | | 42 | Pribosomal protein replication factor, *Helicobacter pylori* | ksvhaflk |
| | | | Replication-associated protein *Staph. aureus* | |
| | | 10 | *Mycoplasma pulmonic*, chromosome replication | kkektthnk |
| | | 43 | Macrophage infectivity potentiator, *L. legionella* | kvhffqlkk |
| | | 90 | *Bacillus anthracis* | kihlisvkk |
| | | 91 | *Bacillus anthracis* | hvkekeknk |
| | | 92 | *Bacillus anthracis* | khivkievk |
| | | 93 | *Bacillus anthracis* | kkkikdiygkdallh |
| | | 94 | *Bacillus anthracis* | kwekikqh |
| | | 95 | *Bacillus anthracis* | kklqipiepkkddiih |
| | | 96 | *Bacillus anthracis* | hnryasnivesaylilnewkn-niqsdlikk |
| | | 97 | *Bacillus anthracis* | havddyagylldknqsdlvt-nskk |
| | | 98 | *Bacillus anthracis* | haerlkvqknapk |
| Plants: | | 44 | *Arabidopsis thaliana*, prolifera | kdhdfdgdk |
| | | 45 | *Arabidopsis thaliana*, cytoplasmic ribosomal | kmkglkqkkah |
| | | 46 | *Arabidopsis thaliana*, DNA binding protein | kelssttqeksh |
| | | 37 | Oryza sativa | kkaygnelhk |
| Viruses: | | 9 | Replication associated protein A [Maize streak virus] | kekkpskdeimrdiish |
| | | 11 | Bovine herpes virus 4, DNA replication protein | hkinitngqk |
| | | 12 | Meleagrid herpesvirus 1, replication binding protein | hkdlyrllmk |
| | | 47 | Feline immunodeficiency | hlkdyklvk |
| | | 3 | Foot and Mouth Disease (O) | hkqkivapvk |
| | | 5 | HIV Type 1 | kcfncgkegh |
| | | 7 | HIV Type 2 | kcwncgkegh |
| | | 99 | Small Pox Virus (Variola) | khynnitwyk |
| | | 100 | Small Pox Virus (Variola) | kysqtgkeliih |
| | | 101 | Small Pox Virus (Variola) | hyddvrikndivvsrck |
| | | 102 | Small Pox Virus (Variola) | hrfklildski |
| | | 103 | Small Pox Virus (Variola) | kerghnyyfek |
| Tumor Viruses: | | 48 | Rous sarcoma virus tyrosine-protein kinase | kklrhek |
| | | 49 | v-yes, avian sarcoma | kklrhdk |
| | | 50 | c-yes, colon cancer, malignant melanoma | kklrhdk |
| | | 51 | v-srcC., avian sarcoma | kklrhek |
| | | 52 | c-src, colon, mammary, panrcreatic cancer | kklrhek |
| | | 53 | Neuroblastoma RAS viral (v-ras) oncogene | kqahelak |
| | | 54 | VP1 (major capsid protein) [Polyamavirus sp.] | kthrfskh |
| | | 55 | Sindbis | knlhekik |
| | | 56 | El [Human papilloamavirus type 71] | khrpllqlk |
| | | 57 | v-erbB from AEV and c-erb | kspnhvk |
| | | 58 | v-fms (feline sarcoma) | knihlekk |
| | | 59 | c-fms (acute and chronic myelomonocytic tumors) | knihlekk |
| | | 60 | large t-antigen I [Polyomavirus sp.l | kphlaqslek |
| | | 61 | middle t-antigen [Polyomavirus sp,l- | kqhrelkdk |
| | | 62 | small t-antigen [Polyomavirus spJ, | kqhrelkdk |
| | | 63 | v-abl, murine acute leukemia | kvpvlisptlkh |
| | | 64 | Human T-cell lymphotropic virus typo 2 | kslllevdkdish |
| | | 65 | c-kit, G1 tumors, small cell lung carcinoma | kagitimvkreyh |
| | | 18 | Hepatitis C | hyppkpgcivpak |
| Trans-forming Proteins: | | 66 | Transforming protein myb | ksgkhlgk |
| | | 67 | Transforming protein myc, Burkitt lymphoma | krreqlkhk |
| | | 68 | Ras-related GTP-binding protein | ksfevikvih |
| | | 69 | Transforming protein ras (teratocarcinoma) | kkkhtvkk |
| | | 70 | TRAF-associated NF-kB activator TANK | kaqkdhlsk |
| | | 71 | RFP transforming protein | hlkrvkdlkk |
| | | 72 | Transforming protein D (S.C.) | kygspkhrlik |
| | | 73 | Papilloma virus type 11, transforming protein | klkhilgkarfik |
| | | 74 | Protein tryosine kinase (EC 2.7.1.ll2slk | kgdhvkhykirk |
| | | 75 | Transforming protein (axl(—)) | keklrdvmvdrhk |
| | | 76 | Transforming protein (N-myc) | klqarqqqllkkieh |
| | | 77 | Fibroblast growth factor 4 (Kaposi sarcoma) | kkgnrvsptmkvth |
| Cancer Cell Proteins: | | 78 | Matrix metaloproteinase 7 (uterine) | keiplhfrk |
| | | 79 | Transcription factor 7-like | kkkphikk |
| | | 80 | Breast cancer antigen NY-BR-87 | ktrhdplak |
| | | 81 | BRCA-1-Associated Ring Domain Protein (breast) | khhpkdnlik |
| | | 82 | 'Autoantigen from a breast tumor' | khkrkkfrqk |
| | | 83 | Glioma replikin (this study) | kagvaflhkk |
| | | 84 | Ovarian cancer antigen | khkrkkfrqk |

TABLE 2-continued

Examples of replikins in various organisms - prototype: Glioma replikin* kagvaflhkk
(SEQ ID No.: 1)

| | | |
|---|---|---|
| 85 | EE L leukemia | kkkskkhkdk |
| 86 | Proto-oncogene tyrosine-protein kinase C-ABLE | hksekpalprk |
| 87 | Adenomatosis polyposis coli | kkkkpsrlkgdnek |
| 88 | Gastric cancer transforming protein | ktkkgnrvsptmkvth |
| 89 | Transforming protein (K-RAS 2B), lung | khkekmskdgkkkkkksk |

Identification of an amino acid sequence as a replikin or as containing a replikin, i.e., a homologue of the malignin 16-mer peptide, requires that the three following "3-point recognition" requirements be met. The peptide sequence must have (1) at least one lysine residue located six to ten residues from another lysine residue; (2) at least one histidine residue; and (3) a composition of at least 6% lysine within an amino acid sequence of 7 to about 50 residues.

Databases were searched using the National Library of Medicine keyword "PubMed" descriptor for protein sequences containing replikin sequences. Sequences of all individual proteins within each group of PubMed-classified proteins were visually scanned for peptides meeting the three above-listed requirements. An infrequent occurrence of homologues was observed in "virus peptides" as a whole (1.5%), and in other peptides not designated as associated with malignant transformation or replication such as "brain peptides" and "neuropeptides" (together 8.5%). Surprisingly, homologues were identified in 100% of "tumor viruses", in 85% of "transforming proteins", and in 97% of "cancer cell proteins" (FIG. 1). The peptides identified by this search were named replikins, and a ten amino acid portion of the 16-mer peptide, (SEQ ID NO.: 1) "kagvaflhkk", was named the glioma replikin.

To permit classification of subtypes of replikins, additional or "auxiliary specifications" to the basic "3-point-recognition" requirements may be added: (a) on a structural basis, such as the common occurrence of adjacent di- and polylysines in cancer cell proteins (e.g., Transforming protein P21B(K-RAS 2B), lung, Table 2, SEQ ID NO.: 89), and other adjacent di-amino acids in TOLL-like receptors, or b) on a functional basis, such as exhibiting ATPase, tyrosine kinase or redox activity as seen in Table 2.

Whether replikin structures are conserved or are subject to extensive natural mutation was examined by scanning the protein sequences of various isolates of foot and mouth disease virus (FMDV), where mutations in proteins of these viruses have been well documented worldwide for decades. Protein sequences of FMDV isolates were visually examined for the presence of both the entire replikin and each of the component replikin amino acid residues observed in a particular replikin. For example, in the protein VP1 of FMDV type O, the replikin (SEQ ID NO.: 3) "hkqkivapvk" was found to be conserved in 78% of the 236 isolates reported in PubMed, and each amino acid was found to be conserved in individual isolates as follows: his, 95.6%; lys, 91.8%; gln 92.3%; lys, 84.1%; ile, 90.7%; val, 91.8%; ala, 97.3%; pro, 96.2%; ala, 75.4%; and lys, 88.4%. The high rate of conservation suggests structural and functional stability of the replikin structure. Similarly, sequence conservation was observed in different isolates of HIV for its replikins, such as (SEQ ID NO.: 5) "kcfncgkegh" or (SEQ ID NO.: 6) "kvylawvpahk" in HIV Type 1 and (SEQ ID NO.: 7) "kcwncgkegh" in HIV Type 2 (Table 2). Other examples of conservation are seen in the constant presence of malignin in successive generations, over 10 years of tissue culture of glioma cells, and by the constancy of affinity of the glioma replikin for antimalignin antibody isolated by immunoadsorption from 8,090 human sera from the U.S., U.K., Europe and Asia (e.g., FIG. 5 and U.S. Pat. No. 6,242,578 B 1).

Figure 2:
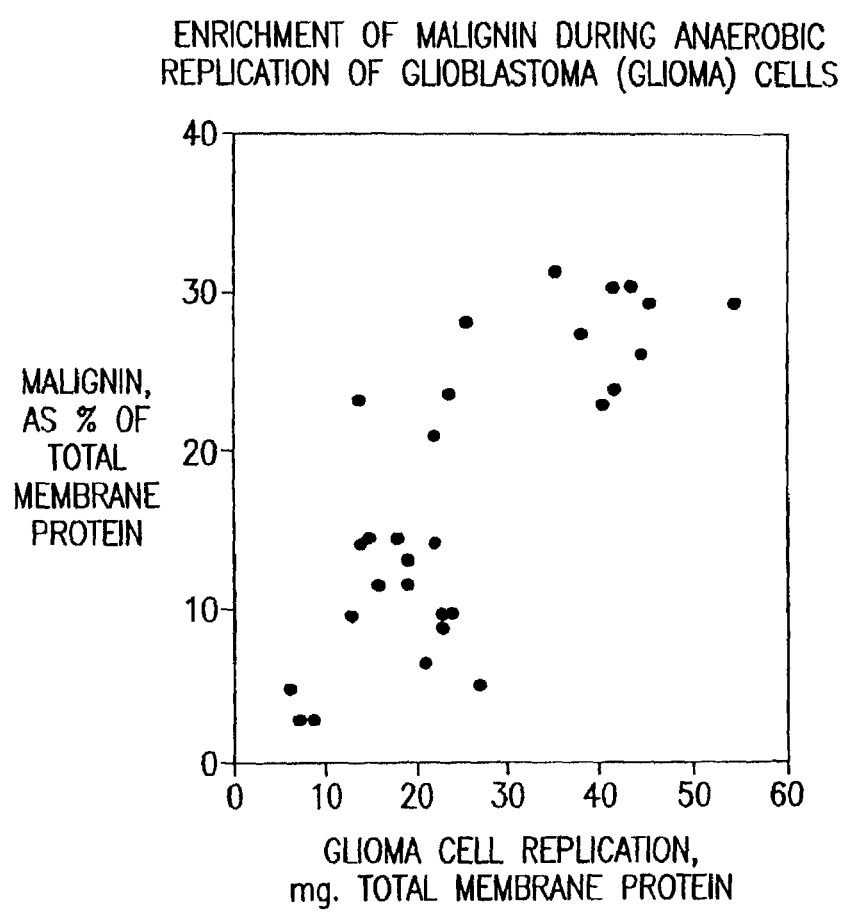
FIG. 2 is a graph depicting the percentage of malignin per milligram total membrane protein during anaerobic replication of glioblastoma cells.

As seen in FIG. 2, during anaerobic respiration when the rate of cell replication is increased, malignin is enriched. That is, malignin is found to increase not simply in proportion to the increase in cell number and total membrane proteins, but is enriched as much as tenfold in concentration, starting with 3% at rest and reaching 30% of total membrane protein. This clear demonstration of a marked increase in replikin concentration with glioma cell replication points to and is consistent with the presence of replikins here sought by the 3-point recognition method and found in the proteins of various organisms which were found by mutation studies and other previous studies to be critical to replication. For example, replikins were identified in such proteins as "*Saccharomyces cerevisiae* replication binding protein" (SEQ ID NO.: 2) (hsikrelgiifdk); the "replication associated protein A of maize streak virus" (SEQ ID NO.: 8) (kyivcareahk and (SEQ ID NO.: 9) kekkpskdeimrdiish); the "replication-associated protein of *Staphylococcus aureus*" (SEQ ID NO.: 10) (kkektthnk); the "DNA replication protein of bovine herpes virus 4" (SEQ ID NO.: 11) (hkinitngqk); and the "Mealigrid herpes virus 1 replication binding protein" (SEQ ID NO.: 12) (hkdlyrllmk). Previous studies of tomato leaf curl gemini virus show that the regulation of virus accumulation appears to involve binding of amino acids 1-160 of the "replicating protein" of that virus to leaf DNA and to other replication protein molecules during virus replication. Analysis of this sequence showed that amino acids 1-163 of this "replicating protein" contain five replikins, namely: (SEQ ID NO.: 13) kfrinaknyfltyph, (SEQ ID NO.: 14) knletpvnklfiricrefh, (SEQ ID NO.: 15) hpniqaaksstdvk, (SEQ ID NO.: 16) ksstdvkaymdkdgdvldh, and (SEQ ID NO.: 17) kasalnilrekapkdfvlqfh.

Table 2 shows that replikin-containing proteins also are associated frequently with redox functions, and protein synthesis or elongation, as well as with cell replication. The association with metal-based redox functions, the enrichment of the replikin-containing glioma malignin concentration during anaerobic replication, and the cytotoxicity of antimalignin at low concentrations (picograms/cell) (FIG. 4c-f), all suggest that the replikins are related to central respiratory functions, which are perhaps less often subjected to the mutations characteristic of proteins of more superficial location or less central survival function.

Of particular interest were eight different replikins identified in *Bacillus anthracis*, the organism responsible for anthrax infections; and five different replikins identified in small pox virus. The eight *Bacillus anthracis* peptides are present in the Anthrax Toxin Lethal Factor Protein pX01-107 and have the amino acid sequence of SEQ ID NO. 91, SEQ ID NO. 92, SEQ ID NO. 93, SEQ ID NO. 94, SEQ ID NO. 95, SEQ ID NO. 96, SEQ ID NO. 97 and SEQ ID NO. 98, respectively. The five small pox virus peptides are present in the Small Pox Virus Surface Antigen S Precursor Protein, which purportedly enhances Small Pox Virus replication. The five peptides have the amino acid sequence of SEQ ID NO. 99, SEQ ID NO. 100, SEQ ID NO. 101, SEQ ID NO. 102 and SEQ ID NO. 103, respectively.

Figure 3:
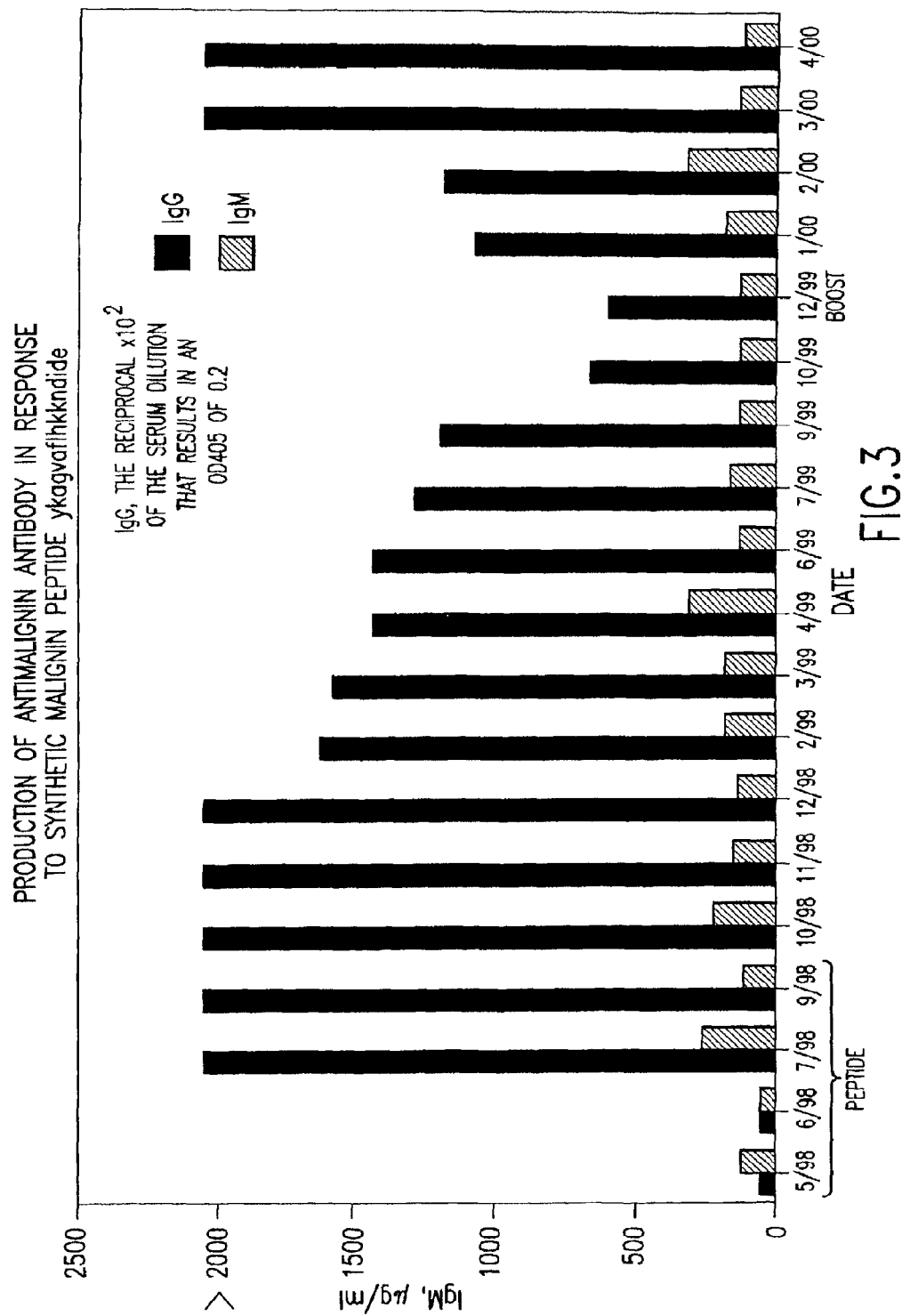
FIG. 3 is a bar graph showing amount of antimalignin antibody produced in response to exposure to the recognin 16-mer.

Data on anti-replikin antibodies support replikin class unity. An anti-replikin antibody response has been quantified by immunoadsorption of serum antimalignin antibody to immobilized malignin (see Methods in U.S. Pat. No. 5,866, 690). The abundant production of antimalignin antibody by administration to rabbits of the synthetic version of the 16-mer peptide whose sequence was derived from malignin, absent carbohydrate or other groups, has established rigorously that this peptide alone is an epitope, that is, it is a sufficient basis for this immune response (FIG. 3). The 16-mer peptide produced both IgM and IgG forms of the antibody. Antimalignin antibody was found to be increased in concentration in serum in 37% of 79 cases in the U.S. and Asia of hepatitis B and C, early, in the first five years of infection, long before the usual observance of liver cancer, which develops about fifteen to twenty-five years after infection. Relevant to both infectious hepatitis and HIV infections, transformed cells may be one form of safe haven for the virus: prolonging cell life and avoiding virus eviction, so that the virus remains inaccessible to anti-viral treatment.

A synthetic replikin vaccine such as the glioma replikin (SEQ ID NO.: 1) "kagvaflhkk" or the hepatitis C replikin (SEQ ID NO.: 18) "hyppkpgcivpak", or HIV replikins such as (SEQ ID NO.: 5) "kcfncgkegh" or (SEQ ID NO.: 6) "kvylawvpahk" may be used to augment antibody concentration in order to lyse the respective virus infected cells and release virus extracellularly where chemical treatment can then be effective. Recognin and/or replikin peptides may be administered to a subject to induce the immune system of the subject to produce anti-replikin and/or anti-recognin antibodies. Generally, a 0.5 to about 2 mg dosage, preferably a 1 mg dosage of each peptide is administered to the subject to induce an immune response. Subsequent dosages may be administered if desired.

In another embodiment of the invention, isolated recognin or replikin peptides may be used to generate antibodies. Various procedures known in the art may be used for the production of antibodies to replikin sequences or recognin sequences. Such antibodies include but are not limited to polyclonal, monoclonal, chimeric, humanized, single chain, Fab fragments and fragments produced by an Fab expression library. Antibodies that are linked to a cytotoxic agent may also be generated.

For the production of antibodies various host animals may be immunized by injection with a replikin or recognin peptide, including but not limited to rabbits, mice, rats, and larger mammals. Various adjuvants may be used to enhance the immunological response, depending on the host species, including but not limited to Freund's (complete and incomplete), mineral gels, such as aluminum hydroxide, surface active substances such as lysolecithin, pluronic polyols, polyanions, peptides, oil emulsions, key limpet hemocyanin, dintrophenol, and potentially useful human adjuvants such as BCG and *Corynebacterium parvum*.

Monoclonal antibodies to replikins or recognins may be prepared by using any technique that provides for the production of antibody molecules by continuous cell lines in culture. These include but are not limited to the hybridoma technique originally described by Kohler and Milstein, (Nature, 1975, 256:495-497), the human B-cell hybridoma technique (Kosbor et al., 1983, Immunology Today, 4:72), and the EBV hybridoma technique (Cole et al., Monoclonal Antibodies and Cancer Therapy, Alan R. Liss, Inc., pp. 77-96). In addition, techniques developed for the production of chimeric antibodies (Morrison et al., 1984, Proc. Nat. Acad. Sci USA, 81:6851-6855) may be used. Alternatively, techniques described for the production of single chain antibodies (U.S. Pat. No. 4,946,778) can be adapted to produce replikin- or recognin-specific single chain antibodies.

Particularly useful antibodies of the invention are those that specifically bind to replikin sequences contained in peptides and/or polypeptides of *Bacillus anthracis*. For example, antibodies to any of peptides SEQ ID NO. 91, SEQ ID NO:92, SEQ ID NO. 93, SEQ ID NO. 94, SEQ ID NO. 95, SEQ ID NO. 96, SEQ ID NO. 97, SEQ ID NO. 98 and combinations of such antibodies are useful in the treatment and/or prevention of anthrax.

Similarly, antibodies to peptides SEQ ID NO. 99, SEQ ID NO. 100, SEQ ID NO. 101, SEQ ID NO. 102, SEQ ID NO. 103 and combinations of such antibodies are useful in the treatment and/or prevention of small pox.

Antibody fragments which contain binding sites for a replikin or recognin may be generated by known techniques. For example, such fragments include but are not limited to $F(ab')_2$ fragments which can be produced by pepsin digestion of the antibody molecules and the Fab fragments that can be generated by reducing the disulfide bridges of the $F(ab')_2$ fragments. Alternatively, Fab expression libraries can be generated (Huse et al., 1989, Science, 246:1275-1281) to allow rapid and easy identification of monoclonal Fab fragments with the desired specificity.

Figure 4A:
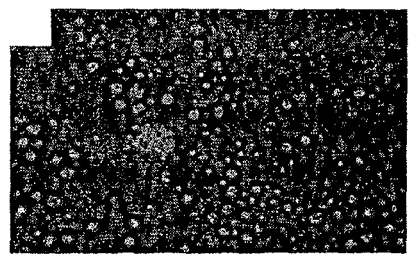
FIG. 4A is a photograph of a blood smear taken with ordinary and fluorescent light.
Figure 4B:
FIG. 4B is a photograph of a blood smear taken with and fluorescent light illustrating the presence of two leukemic cells.
Figure 4C:
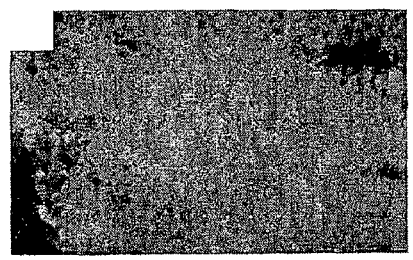
FIG. 4C is a photograph of a dense layer of glioma cells in the presence of antimalignin antibody.
Figure 4D:
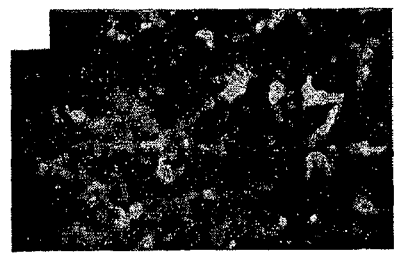
FIG. 4D and FIG. 4E are photographs of the layer of cells in FIG. 4C taken at 30 and 45 minutes following addition of antimalignin antibody.
Figure 4E:
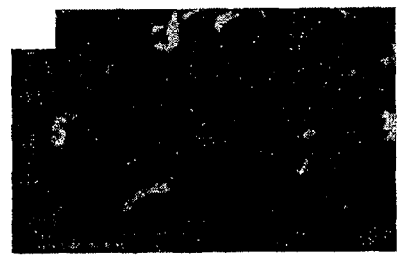
Figure 4F:
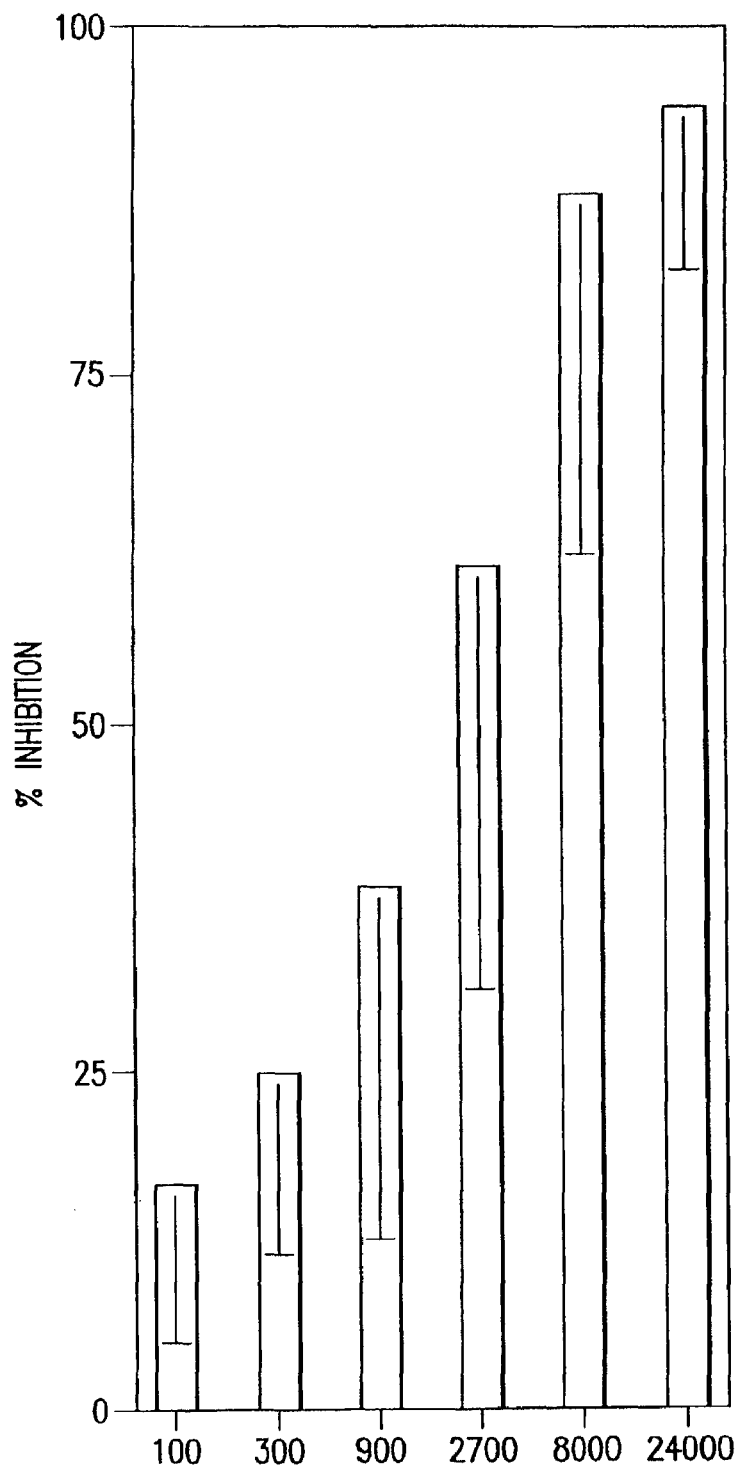
FIG. 4F is a bar graph showing the inhibition of growth of small cell lung carcinoma cells in vitro by antimalignin antibody.

The fact that antimalignin antibody is increased in concentration in human malignancy regardless of cancer cell type (FIG. 5), and that this antibody binds to malignant cells regardless of cell type now may be explained by the presence of the replikin structures present in most malignancies (FIG. 1 and Table 2). Population studies have shown that antimalignin antibody increases in concentration in healthy adults with age, and more so in high-risk families, as the frequency of cancer increases. An additional two-fold or greater antibody increase which occurs in early malignancy has been independently confirmed with a sensitivity of 97% in breast cancers 1-10 mm in size. Shown to localize preferentially in malignant cells in vivo, histochemically the antibody does not bind to normal cells but selectively binds to (FIG. 4*a,b*) and is highly cytotoxic to transformed cells in vitro (FIG. 4*c-f*). Since in these examples the same antibody is bound by several cell types, that is, brain glioma, hematopoietic cells (leukemia), and small cell carcinoma of lung, malignant replikin class unity is again supported.

Figure 5:
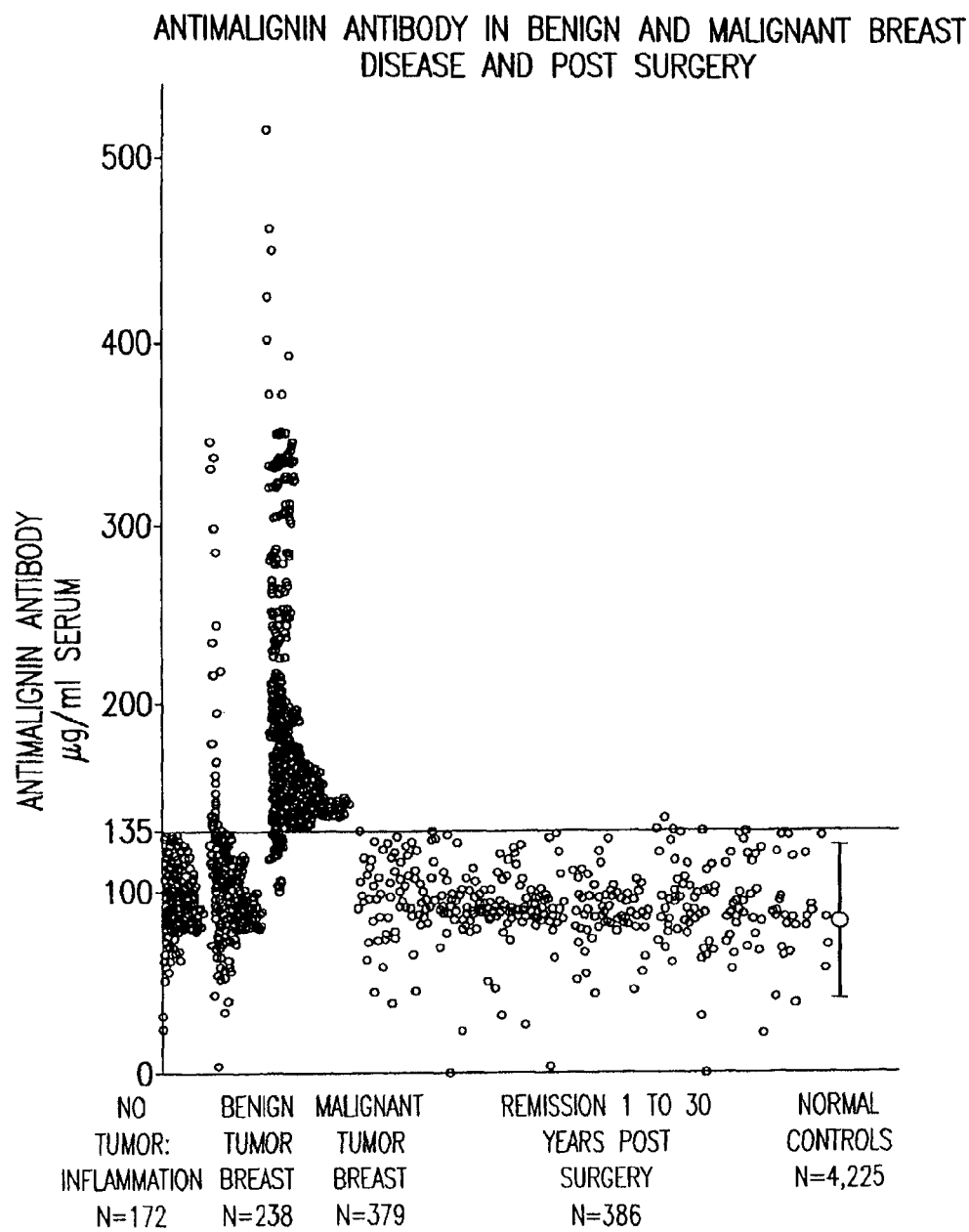
FIG. 5 is a plot of the amount of antimalignin antibody present in the serum of patients with benign or malignant breast disease pre- and post surgery.

Antimalignin does not increase with benign proliferation, but specifically increases only with malignant transformation and replication in breast in vivo and returns from elevated to normal values upon elimination of malignant cells (FIG. 5). Antimalignin antibody concentration has been shown to relate quantitatively to the survival of cancer patients, that is, the more antibody, the longer the survival. Taken together, these results suggest that antireplikin antibodies may be a part of a mechanism of control of cell transformation and replication. Augmentation of this immune response may be useful in the control of replication, either actively with synthetic replikins as vaccines, or passively by the administration of anti-replikin antibodies, or by the introduction of non-immune based organic agents, such as for example, carbohydrates, lipids and the like, which are similarly designed to target the replikin specifically. For organisms such as diatom plankton, foot and mouth disease virus, tomato leaf curl gemini virus, hepatitis B and C, and HIV, and malignant cells, identified constituent replikins are useful as vaccines, and also may be usefully targeted for diagnostic purposes.

The replikin sequence structure is associated with the function of replication. Thus, whether the replikins of this invention are used for targeting sequences that contain replikins for the purpose of diagnostic identification, promoting replication, or inhibiting or attacking replication, for example, the structure-function relationship of the replikin is fundamental. Thus, while the structure of the replikin may be a part of a larger protein sequence, which may have been previously identified, it is necessary to utilize only the specific replikin structure when seeking to induce antibodies that will recognize and attach to the replikin fragment and thereby cause destruction of the cell. Even though the larger protein sequence may be known in the art as having a "replication associated function," vaccines using the larger protein often have failed or proven ineffective, even though they contain one or more replikin sequences.

Although the present inventors do not wish to be held to a single theory, the studies herein suggest that the prior art vaccines are ineffective because they are based on the use of the larger protein sequence. The larger protein sequence invariably has one or more epitopes (independent antigenic sequences that can induce specific antibody formation); replikin structures usually comprise one of these potential epitopes. The presence of other epitopes within the larger protein may interfere with adequate formation of antibodies to the replikin, See, e.g., Webster, R. G., J. Immunol., 97(2): 177-183 (1966); and Webster et al., J. Infect. Dis., 134:48-58, 1976; Klenerman et al, Nature 394:421-422 (1998) for a discussion of the well-known phenomenon "original antigenic sin"). The formation of an antibody to a non-replikin epitope may allow binding to the cell, but not necessarily lead to cell destruction.

It is well known in the art that in the course of antibody production against a "foreign" protein, the protein is first hydrolyzed into smaller fragments. Usually fragments containing from about six to ten amino acids are selected for antibody formation. Thus, if hydrolysis of a protein does not result in replikin-containing fragments, anti-replikin antibodies will not be produced. In this regard, it is interesting that replikins contain lysine residues located six to ten amino acids apart, since lysine residues are known to bind to membranes.

Furthermore, replikin sequences contain at least one histidine residue. Histidine is frequently involved in binding to redox centers. Thus, an antibody that specifically recognizes a replikin sequence has a better chance of inactivating or destroying the cell in which the replikin is located, as seen with anti-malignin antibody, which is perhaps the most cytotoxic antibody yet described, being active at picograms per cell.

One of the reasons that vaccines directed towards a particular protein antigen of a disease causing agent have not been fully effective in providing protection against the disease (such as foot and mouth vaccine which has been developed against the VP1 protein or large segments of the VP1 protein) is that antibody to the replikins have not been produced. That is, either epitopes other than replikins present in the larger protein fragments may interfere according to the phenomenon of "original antigenic sin", and/or because the hydrolysis of larger protein sequences into smaller sequences for processing to produce antibodies results in loss of integrity of any replikin structure that is present, e.g., the replikin is cut in two and/or the histidine residue is lost in the hydrolytic processing. The present studies suggest that for an effective vaccine to be produced, the replikin sequences, and no other epitope, should be used as the vaccine. For example, a vaccine of the invention can be generated using any one of the replikin peptides identified by the three point recognition system. Particularly preferred peptides for an anthrax vaccine include peptides SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, and combinations thereof. Preferred peptides for use as a small pox vaccine are peptides SEQ ID NO. 99, SEQ ID NO. 100, SEQ ID NO. 101, SEQ ID NO. 102, SEQ ID NO. 103 and combinations thereof. These peptides, alone or in various combinations are administered to a subject, preferably by i.v. or intramuscular injection, in order to stimulate the immune system of the subject to produce antibodies to the peptide. Generally the dosage of peptides is in the range of from about 0.1 µg to about 10 mg, preferably about 10 µg to about 1 mg, and most preferably about 50 µg to about 500 ug. The skilled practitioner can readily determine the dosage and number of dosages needed to produce an effective immune response.

Replikin or recognin DNA or RNA may have a number of uses for the diagnosis of diseases resulting from infection with a virus, bacterium or other replikin or recognin encoding agent. For example, replikin or recognin nucleotide sequences may be used in hybridization assays of biopsied tissue to diagnose the presence of a particular organism, e.g., Southern or Northern analysis, including in situ hybridization assays.

Also within the scope of the invention are oligoribonucleotide sequences, that include antisense RNA and DNA molecules and ribozymes that function to inhibit the translation of replikin- or recognin-containing mRNA. Both antisense RNA and DNA molecules and ribozymes may be prepared by any method known in the art. The antisense molecules can be incorporated into a wide variety of vectors for delivery to a subject. The skilled practitioner can readily determine the best route of delivery, although generally i.v. or i.m. delivery is routine. The dosage amount is also readily ascertainable.

Particularly preferred antisense nucleic acid molecules are those that are complementary to a mRNA encoding a *Bacillus anthracis* polypeptide comprising a replikin sequence comprising from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to the coding strand of the gene or to the mRNA encoding the *Bacillus anthracis* Anthrax Lethal Factor Protein pX01-107 peptide, wherein the antisense nucleic acid molecule is complementary to a nucleotide sequence encoding the peptide of SEQ ID NO. 91, SEQ ID NO. 92, SEQ ID NO. 93, SEQ ID NO. 94, SEQ ID NO. 95, SEQ ID NO. 96, SEQ ID NO. 97, or SEQ ID NO. 98.

Another preferred set of antisense nucleic acid molecules includes those that are complementary to a mRNA encoding a Small Pox Virus polypeptide comprising a replikin sequence comprising from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to the coding strand of the gene or to the mRNA encoding the Small Pox Virus Surface Antigen S Precursor Protein, wherein the antisense nucleic acid molecule is complementary to a nucleotide sequence encoding the peptide of SEQ ID NO. 99, SEQ ID NO. 100, SEQ ID NO. 101, SEQ ID NO. 102, or SEQ ID NO. 103.

In another embodiment of the invention, immune serum containing antibodies to one or more replikin obtained from an individual exposed to one or more replikins may be used to induce passive immunity in another individual or animal.

Immune serum may be administered via i.v. to a subject in need of treatment. Passive immunity also can be achieved by injecting a recipient with preformed antibodies to one or more replikins. Passive immunization may be used to provide immediate protection to individuals who have been exposed to an infectious organism. Administration of immune serum or preformed antibodies is routine and the skilled practitioner can readily ascertain the amount of serum or antibodies needed to achieve the desired effect.

Visual scanning of over three thousand sequences was performed in developing the present 3-point-recognition methods. However, data banks comprising nucleotide and/or amino acid sequences can also be scanned by computer for the presence of sequences meeting the 3 point recognition requirements.

The three point recognition method may also be modified to identify other useful compounds of covalently linked organic molecules, including other covalently linked amino acids, nucleotides, carbohydrates, lipids or combinations thereof. In this embodiment of the invention a sequence is screened for subsequences containing three or more desired structural characteristics. In the case of screening compounds composed of covalently linked amino acids, lipids or carbohydrates the subsequence of 7 to about 50 covalently linked units should contain (1) at least one first amino acid, carbohydrate or lipid residue located six to ten residues from a second of the first amino acid, carbohydrate or lipid residue; (2) at least one second amino acid, lipid or carbohydrate residue; and (3) at least 6% of the first amino acid, carbohydrate or lipid residue. In the case of screening nucleotide sequences, the subsequence of about 21 to about 150 nucleotides should contain (1) at least one first amino acid residue located within eighteen to thirty nucleotides from a second codon encoding the first amino acid residue; (2) at least one second amino acid residue; and (3) encodes at least 6% of said first amino acid residue.

Figure 6:
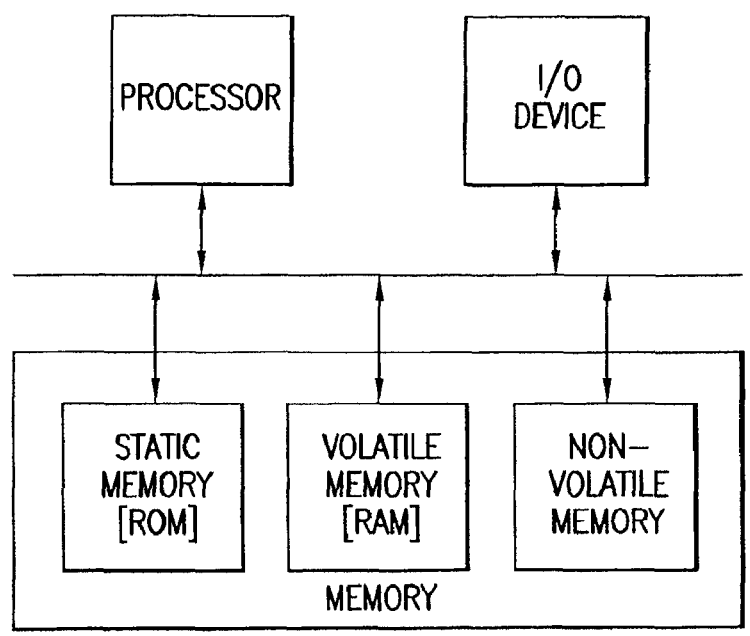
FIG. 6 is a box diagram depicting an embodiment of the invention wherein a computer is used to carry out the 3-point-recognition method of identifying replikin and recognin sequences.

According to another embodiment of the invention, the methods described herein may be performed by a computer. FIG. 6 is a block diagram of a computer available for use with the foregoing embodiments of the present invention. The computer may include a processor, an input/output device and a memory storing executable program instructions representing the 3-point-recognition methods of the foregoing embodiments. The memory may include a static memory, volatile memory and/or a nonvolatile memory. The static memory conventionally may be a read only memory ("ROM") provided on a magnetic, or an electrical or optical storage medium. The volatile memory conventionally may be a random access memory ("RAM") and may be integrated as a cache within the processor or provided externally from the processor as a separate integrated circuit. The non-volatile memory may be an electrical, magnetic or optical storage medium.

Example 1

Process for Extraction, Isolation and Identification of Replikins and the Use of Replikins to Target, Label or Destroy Replikin-Containing Organisms a) Algae The following algae were collected from Bermuda water sites and either extracted on the same day or frozen at −20 degrees C. and extracted the next day. The algae were homogenized in a cold room (at 0 to 5 degrees C.) in 1 gram aliquots in neutral buffer, for example 100 cc. of 0.005M phosphate buffer solution, pH7 ("phosphate buffer") for 15 minutes in a Waring blender, centrifuged at 3000 rpm, and the supernatant concentrated by perevaporation and dialyzed against phosphate buffer in the cold to produce a volume of approximately 15 ml. The volume of this extract solution was noted and an aliquot taken for protein analysis, and the remainder was fractionated to obtain the protein fraction having a pK range between 1 and 4. The preferred method of fractionation is chromatography as follows:

The extract solution is fractionated in the cold room (4 degrees C.) on a DEAE cellulose (Cellex-D) column 2.5× 11.0 cm, which has been equilibrated with 0.005M phosphate buffer. Stepwise eluting solvent changes are made with the following solutions:

Solution 1—4.04 g. NaH2P04 and 0.5 g NaH2P04 are dissolved in 15 liters of distilled water (0.005 molar, pH7);

Solution 2—8.57 g. NaH2P04 is dissolved in 2,480 ml. of distilled water;

Solution 3—17.1 g. of NaH2P04 is dissolved in 2480 ml of distilled water (0.05 molar, pH 4.7);

Solution 4—59.65 g. of NaH2P04 is dissolved in 2470 ml distilled water (0.175 molar);

Solution 5—101.6 g. of NaH2P04 is dissolved in 2455 ml distilled water (pH 4.3);

Solution 6—340.2 g. of NaH2P04 is dissolved in 2465 of distilled water (1.0 molar, pX-i 4.1);

Solution 7—283.63 g. of 80% phosphoric acid (H3PO4) is made up in 2460 ml of distilled water (1.0 molar, pH 1.0).

The extract solution, in 6 to 10 ml volume, is passed onto the column and overlayed with Solution 1, and a reservoir of 300 ml of Solution 1 is attached and allowed to drip by gravity onto the column. Three ml aliquots of eluant are collected and analyzed for protein content at OD 280 until all of the protein to be removed with Solution 1 has been removed from the column. Solution 2 is then applied to the column, followed in succession by Solutions 3, 4, 5, 6 aid 7 until all of the protein which can, be removed with each Solution is removed from the column. The eluates from Solution 7 are combined, dialyzed against phosphate buffer, the protein content determined of both dialysand and dialyzate, and both analyzed by gel electrophoresis. One or two bands of peptide or protein of molecular weight between 3,000 and 25,000 Daltons are obtained in Solution 7. For example the algae *Caulerpa mexicana, Laurencia obtura, Cladophexa prolifera, Sargassum natans, Caulerpa verticillata, Halimeda tuna,* and *Penicillos capitatus*, after extraction and treatment as above, all demonstrated in Solution 7 eluates sharp peptide bands in this molecular weight region with no contaminants. These Solution 7 proteins or their eluted bands are hydrolyzed, and the amino acid composition determined. The peptides so obtained, which have a lysine composition of 6% or greater are Replikin precursors. These Replikin peptide precursors are then determined for amino acid sequence by hydrolysis and mass spectrometry as detailed in U.S. Pat. No. 6,242,578 B1. Those which fulfill the criteria defined by the "3-point-recognition" method are identified as Replikins. This procedure can also be applied to obtain yeast, bacterial and any plant Replikins.

b) Virus

Using the same extraction and column chromatography separation methods as above in a) for algae, Replikens in virus-infected cells are isolated and identified.

c) Tumor Cells In Vivo and In Vitro Tissue Culture

Using the same extraction and column chromatography separation methods as above in a) for algae, Replikins in tumor cells are isolated and identified. For example, Replikin precursors of Astrocytin isolated from malignant brain tumors, Malignin (Aglyco 1OB) isolated from glioblastoma tumor cells in tissue culture, MCF7 mammary carcinoma cells in tissue culture, and P₃J Lymphoma cells in tissue culture each treated as above in a) yielded Replikin precursors with lysine content of 9.1%, 6.7%, 6.7%, and 6.5% respectively. Hydrolysis and mass spectrometry of Aglyco 1OB as described in Example 10 U.S. Pat. No. 6,242,578 B1 produced the amino acid sequence, ykagvaflhkkndiide the 16-mer Replikin.

Example 2

As an example of diagnostic use of Replikins: Aglyco 1OB or the 16-mer Repliken may be used as antigen to capture and quantify the amount of its corresponding antibody present in serum for diagnostic purposes are as shown in FIGS. 2,3,4 and 7 of U.S. Pat. No. 6,242,578 B1, As an example of the production of agents to attach to Replikins for labeling, nutritional or destructive purposes: Injection of the 16-mer Replikin into rabbits to produce the specific antibody to the 16-mer Replikin is shown in Example 6 and FIGS. 9A and 9B of U.S. Pat. No. 6,242,578 B1.

As an example of the use of agents to label Replikins: The use of antibodies to the 16-mer Replikin to label specific cells which contain this Replikin is shown in FIG. 5 and Example 6 of U.S. Pat. No. 6,242,578 B1.

As an example of the use of agents to destroy Replikins: The use of antibodies to the 16-mer Replikin to inhibit or destroy specific cells which contain this Replikin is shown in FIG. 6 of U.S. Pat. No. 6,242,578 B1.

From a proteomic point of view the construction of a "3-point recognition" template based on the new glioma peptide sequence led directly to identification of a biology-wide class of proteins having related structures and functions. The operation of the 3-point-recognition method resembles identification by the use of a "keyword" search; but instead of using the exact spelling of the keyword "kagvafihkk" as in a typical sequence homology search, or in the nucleotide specification of an amino acid, an abstraction of the keyword delimited by the "3-point-recognition" parameters is used. This delimited abstraction, although derived from a single relatively short amino acid sequence leads to identification of a class of proteins with structures that are defined by the same specifications. That particular functions, in this case transformation and replication, in addition to structures, turn out also to be shared by members of the exposed class suggests that these structures and functions are related. Thus, from this newly identified short peptide sequence, a molecular recognition 'language' has been formulated, which previously has not been described. Further, the sharing of immunological specificity by diverse members of the class, as here demonstrated for the cancer replikins, suggests that B cells and their product antibodies recognize replikins by means of a similar recognition language. Since "3-point-recognition" is a proteomic method that specifies a particular class of proteins, using three or more different recognition points for other peptides similarly should provide useful information concerning other proteins classes. Further, the "3-point-recognition" method is applicable to other recognins, for example to the TOLL 'innate' recognition of lipopolyssacharides of organisms.

Several embodiments of the present invention are specifically illustrated and described herein. However, it will be appreciated that modifications and variations of the present invention are encompassed by the above teachings and within the purview of the appended claims without departing from the spirit and intended scope of the invention.

What is claimed is:

1. An isolated antibody that specifically binds to a peptide sequence from an Anthrax Toxin Lethal Factor protein pX01-107, wherein said peptide consists of 7 to about 50 amino acids with at least one lysine residue on one end of the peptide sequence and at least one lysine residue or at least one histidine residue on the other end of the peptide sequence and comprises:
   (1) at least one lysine residue located six to ten amino acid residues from a second lysine residue;
   (2) at least one histidine residue; and
   (3) at least 6% lysine residues.

2. An antibody cocktail comprising a plurality of isolated antibodies of claim 1.

3. A composition comprising the isolated antibody of claim 1 and a pharmaceutically acceptable carrier and/or adjuvant.

4. A composition comprising the antibody cocktail of claim 2 and a pharmaceutically acceptable carrier and/or adjuvant.

5. The isolated antibody of claim 1 wherein the n-terminus of said peptide sequence is a lysine residue and the c-terminus of said peptide sequence is a lysine residue.

6. The isolated antibody of claim 1 wherein the n-terminus of said peptide sequence is a histidine residue and the c-terminus of said peptide sequence is a lysine residue.

7. The isolated antibody of claim 1 wherein the n-terminus of said peptide sequence is a lysine residue and the c-terminus of said peptide sequence is a histidine residue.

8. The isolated antibody of claims 6 or 7 wherein said peptide sequence comprises no more than two lysine residues.

9. The isolated antibody of claim 6 or 7 wherein said peptide sequence comprises no more than one histidine residue.

10. The isolated antibody of claim 1 wherein said peptide sequence comprises at least one of the peptide sequences of SEQ ID NO(s): 91-98.

11. The isolated antibody of claim 1 wherein said peptide sequence consists of one of the peptide sequences of SEQ ID NO(s): 91-98.

12. The isolated antibody of claim 11 wherein said peptide sequence consists of SEQ ID NO: 91.

13. The isolated antibody of claim 11 wherein said peptide sequence consists of SEQ ID NO: 92.

14. The isolated antibody of claim 11 wherein said peptide sequence consists of SEQ ID NO: 93.

15. The isolated antibody of claim 11 wherein said peptide sequence consists of SEQ ID NO: 94.

16. The isolated antibody of claim 11 wherein said peptide sequence consists of SEQ ID NO: 95.

17. The isolated antibody of claim 11 wherein said peptide sequence consists of SEQ ID NO: 96.

18. The isolated antibody of claim 11 wherein said peptide sequence consists of SEQ ID NO: 97.

19. The isolated antibody of claim 11 wherein said peptide sequence consists of SEQ ID NO: 98.

* * * * *

SEQUENCE LISTING

```
<160> NUMBER OF SEQ ID NOS: 103

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      glioma replikin peptide

<400> SEQUENCE: 1

Lys Ala Gly Val Ala Phe Leu His Lys Lys
1               5                   10

<210> SEQ ID NO 2
<211> LENGTH: 13
<212> TYPE: PRT
<213> ORGANISM: Saccharomyces cerevisiae

<400> SEQUENCE: 2

His Ser Ile Lys Arg Glu Leu Gly Ile Ile Phe Asp Lys
1               5                   10

<210> SEQ ID NO 3
<211> LENGTH: 10
<212> TYPE: PRT
<213> ORGANISM: Gemini vinis virus
```

```
<400> SEQUENCE: 3

His Lys Gln Lys Ile Val Ala Pro Val Lys
1               5                   10

<210> SEQ ID NO 4
<211> LENGTH: 16
<212> TYPE: PRT
<213> ORGANISM: Unknown
<220> FEATURE:
<223> OTHER INFORMATION: Description of Unknown: Virus
      recognin peptide

<400> SEQUENCE: 4

Tyr Lys Ala Gly Val Ala Phe Leu His Lys Lys Asn Asp Ile Asp Glu
1               5                   10                  15

<210> SEQ ID NO 5
<211> LENGTH: 10
<212> TYPE: PRT
<213> ORGANISM: Human immunodeficiency virus type 1

<400> SEQUENCE: 5

Lys Cys Phe Asn Cys Gly Lys Glu Gly His
1               5                   10

<210> SEQ ID NO 6
<211> LENGTH: 11
<212> TYPE: PRT
<213> ORGANISM: Human immunodeficiency virus type 1

<400> SEQUENCE: 6

Lys Val Tyr Leu Ala Trp Val Pro Ala His Lys
1               5                   10

<210> SEQ ID NO 7
<211> LENGTH: 10
<212> TYPE: PRT
<213> ORGANISM: Human immunodeficiency virus type 2

<400> SEQUENCE: 7

Lys Cys Trp Asn Cys Gly Lys Glu Gly His
1               5                   10

<210> SEQ ID NO 8
<211> LENGTH: 11
<212> TYPE: PRT
<213> ORGANISM: Maize streak virus

<400> SEQUENCE: 8

Lys Tyr Ile Val Cys Ala Arg Glu Ala His Lys
1               5                   10

<210> SEQ ID NO 9
<211> LENGTH: 17
<212> TYPE: PRT
<213> ORGANISM: Maize streak virus

<400> SEQUENCE: 9

Lys Glu Lys Lys Pro Ser Lys Asp Glu Ile Met Arg Asp Ile Ile Ser
1               5                   10                  15

His

<210> SEQ ID NO 10
<211> LENGTH: 9
```

```
<212> TYPE: PRT
<213> ORGANISM: Staphylococcus aureus

<400> SEQUENCE: 10

Lys Lys Glu Lys Thr Thr His Asn Lys
1               5

<210> SEQ ID NO 11
<211> LENGTH: 10
<212> TYPE: PRT
<213> ORGANISM: Bovine herpesvirus 4

<400> SEQUENCE: 11

His Lys Ile Asn Ile Thr Asn Gly Gln Lys
1               5                   10

<210> SEQ ID NO 12
<211> LENGTH: 10
<212> TYPE: PRT
<213> ORGANISM: Meleagrid herpesvirus 1

<400> SEQUENCE: 12

His Lys Asp Leu Tyr Arg Leu Leu Met Lys
1               5                   10

<210> SEQ ID NO 13
<211> LENGTH: 15
<212> TYPE: PRT
<213> ORGANISM: Unknown
<220> FEATURE:
<223> OTHER INFORMATION: Description of Unknown: Virus
      recognin peptide

<400> SEQUENCE: 13

Lys Phe Arg Ile Asn Ala Lys Asn Tyr Phe Leu Thr Tyr Pro His
1               5                   10                  15

<210> SEQ ID NO 14
<211> LENGTH: 19
<212> TYPE: PRT
<213> ORGANISM: Unknown
<220> FEATURE:
<223> OTHER INFORMATION: Description of Unknown: Virus
      recognin peptide

<400> SEQUENCE: 14

Lys Asn Leu Glu Thr Pro Val Asn Lys Leu Phe Ile Arg Ile Cys Arg
1               5                   10                  15

Glu Phe His

<210> SEQ ID NO 15
<211> LENGTH: 14
<212> TYPE: PRT
<213> ORGANISM: Unknown
<220> FEATURE:
<223> OTHER INFORMATION: Description of Unknown: Virus
      recognin peptide

<400> SEQUENCE: 15

His Pro Asn Ile Gln Ala Ala Lys Ser Ser Thr Asp Val Lys
1               5                   10

<210> SEQ ID NO 16
<211> LENGTH: 19
<212> TYPE: PRT
<213> ORGANISM: Unknown
<220> FEATURE:
```

<223> OTHER INFORMATION: Description of Unknown: Virus
      recognin peptide

<400> SEQUENCE: 16

Lys Ser Ser Thr Asp Val Lys Ala Tyr Met Asp Lys Asp Gly Asp Val
1               5                   10                  15

Leu Asp His

<210> SEQ ID NO 17
<211> LENGTH: 21
<212> TYPE: PRT
<213> ORGANISM: Unknown
<220> FEATURE:
<223> OTHER INFORMATION: Description of Unknown: Virus
      recognin peptide

<400> SEQUENCE: 17

Lys Ala Ser Ala Leu Asn Ile Leu Arg Glu Lys Ala Pro Lys Asp Phe
1               5                   10                  15

Val Leu Gln Phe His
            20

<210> SEQ ID NO 18
<211> LENGTH: 13
<212> TYPE: PRT
<213> ORGANISM: Hepatitis C virus

<400> SEQUENCE: 18

His Tyr Pro Pro Lys Pro Gly Cys Ile Val Pro Ala Lys
1               5                   10

<210> SEQ ID NO 19
<211> LENGTH: 4
<212> TYPE: PRT
<213> ORGANISM: Homo sapiens

<400> SEQUENCE: 19

Tyr Lys Ala Gly
1

<210> SEQ ID NO 20
<211> LENGTH: 6
<212> TYPE: PRT
<213> ORGANISM: Homo sapiens

<400> SEQUENCE: 20

Tyr Lys Ala Gly Val Ala
1               5

<210> SEQ ID NO 21
<211> LENGTH: 7
<212> TYPE: PRT
<213> ORGANISM: Homo sapiens

<400> SEQUENCE: 21

Tyr Lys Ala Gly Val Ala Phe
1               5

<210> SEQ ID NO 22
<211> LENGTH: 7
<212> TYPE: PRT
<213> ORGANISM: Homo sapiens

<400> SEQUENCE: 22

Tyr Lys Ala Gly Val Ala Phe

-continued

```
<210> SEQ ID NO 23
<211> LENGTH: 9
<212> TYPE: PRT
<213> ORGANISM: Homo sapiens

<400> SEQUENCE: 23

Ala Gly Val Ala Phe His Lys Lys Asn
1               5

<210> SEQ ID NO 24
<211> LENGTH: 4
<212> TYPE: PRT
<213> ORGANISM: Homo sapiens

<400> SEQUENCE: 24

Gly Val Ala Phe
1

<210> SEQ ID NO 25
<211> LENGTH: 3
<212> TYPE: PRT
<213> ORGANISM: Homo sapiens

<400> SEQUENCE: 25

Val Ala Phe
1

<210> SEQ ID NO 26
<211> LENGTH: 7
<212> TYPE: PRT
<213> ORGANISM: Homo sapiens

<400> SEQUENCE: 26

Val Ala Phe Leu His Lys Lys
1               5

<210> SEQ ID NO 27
<211> LENGTH: 7
<212> TYPE: PRT
<213> ORGANISM: Homo sapiens

<400> SEQUENCE: 27

Val Ala Phe Leu His Lys Lys
1               5

<210> SEQ ID NO 28
<211> LENGTH: 9
<212> TYPE: PRT
<213> ORGANISM: Homo sapiens

<400> SEQUENCE: 28

Val Ala Phe Leu His Lys Lys Asn Asp
1               5

<210> SEQ ID NO 29
<211> LENGTH: 8
<212> TYPE: PRT
<213> ORGANISM: Homo sapiens

<400> SEQUENCE: 29

Val Ala Phe His Lys Lys Asn Asp
1               5
```

```
<210> SEQ ID NO 30
<211> LENGTH: 4
<212> TYPE: PRT
<213> ORGANISM: Homo sapiens

<400> SEQUENCE: 30

Ala Phe Leu His
1

<210> SEQ ID NO 31
<211> LENGTH: 8
<212> TYPE: PRT
<213> ORGANISM: Homo sapiens

<400> SEQUENCE: 31

His Lys Lys Asn Asp Ile Asp Glu
1               5

<210> SEQ ID NO 32
<211> LENGTH: 6
<212> TYPE: PRT
<213> ORGANISM: Homo sapiens

<400> SEQUENCE: 32

Lys Lys Asn Asp Ile Asp
1               5

<210> SEQ ID NO 33
<211> LENGTH: 6
<212> TYPE: PRT
<213> ORGANISM: Homo sapiens

<400> SEQUENCE: 33

Lys Asn Asp Ile Asp Glu
1               5

<210> SEQ ID NO 34
<211> LENGTH: 8
<212> TYPE: PRT
<213> ORGANISM: Caldophera prolifera

<400> SEQUENCE: 34

Lys Ala Ser Lys Phe Thr Lys His
1               5

<210> SEQ ID NO 35
<211> LENGTH: 12
<212> TYPE: PRT
<213> ORGANISM: Isolepis prolifera

<400> SEQUENCE: 35

Lys Ala Gln Ala Glu Thr Gly Glu Ile Lys Gly His
1               5                   10

<210> SEQ ID NO 36
<211> LENGTH: 10
<212> TYPE: PRT
<213> ORGANISM: Schizosaccharomyces pombe

<400> SEQUENCE: 36

Lys Ser Phe Lys Tyr Pro Lys Lys His Lys
1               5                   10

<210> SEQ ID NO 37
<211> LENGTH: 10
<212> TYPE: PRT
```

-continued

```
<213> ORGANISM: Oryza sativa

<400> SEQUENCE: 37

Lys Lys Ala Tyr Gly Asn Glu Leu His Lys
1               5                   10

<210> SEQ ID NO 38
<211> LENGTH: 9
<212> TYPE: PRT
<213> ORGANISM: Penicillium marneffei

<400> SEQUENCE: 38

Lys Val Asp Ile Val Thr His Gln Lys
1               5

<210> SEQ ID NO 39
<211> LENGTH: 12
<212> TYPE: PRT
<213> ORGANISM: Diseula destructiva

<400> SEQUENCE: 39

Lys Leu Glu Glu Asp Ala Ala Tyr His Arg Lys Lys
1               5                   10

<210> SEQ ID NO 40
<211> LENGTH: 17
<212> TYPE: PRT
<213> ORGANISM: Ophiostoma novo-ulmi

<400> SEQUENCE: 40

Lys Val Ile Leu Pro Leu Arg Gly Asn Ile Lys Gly Ile Phe Phe Lys
1               5                   10                  15

His

<210> SEQ ID NO 41
<211> LENGTH: 11
<212> TYPE: PRT
<213> ORGANISM: Entamoeba invadens

<400> SEQUENCE: 41

Lys Leu Ile Leu Lys Gly Asp Leu Asn Lys His
1               5                   10

<210> SEQ ID NO 42
<211> LENGTH: 8
<212> TYPE: PRT
<213> ORGANISM: Helicobacter pylori

<400> SEQUENCE: 42

Lys Ser Val His Ala Phe Leu Lys
1               5

<210> SEQ ID NO 43
<211> LENGTH: 9
<212> TYPE: PRT
<213> ORGANISM: Mycoplasma pulmonis

<400> SEQUENCE: 43

Lys Val His Phe Phe Gln Leu Lys Lys
1               5

<210> SEQ ID NO 44
<211> LENGTH: 9
<212> TYPE: PRT
<213> ORGANISM: Arabidopsis thaliana
```

-continued

```
<400> SEQUENCE: 44

Lys Asp His Asp Phe Asp Gly Asp Lys
1               5

<210> SEQ ID NO 45
<211> LENGTH: 11
<212> TYPE: PRT
<213> ORGANISM: Arabidopsis thaliana

<400> SEQUENCE: 45

Lys Met Lys Gly Leu Lys Gln Lys Lys Ala His
1               5                   10

<210> SEQ ID NO 46
<211> LENGTH: 12
<212> TYPE: PRT
<213> ORGANISM: Arabidopsis thaliana

<400> SEQUENCE: 46

Lys Glu Leu Ser Ser Thr Thr Gln Glu Lys Ser His
1               5                   10

<210> SEQ ID NO 47
<211> LENGTH: 9
<212> TYPE: PRT
<213> ORGANISM: Feline immunodeficiency virus

<400> SEQUENCE: 47

His Leu Lys Asp Tyr Lys Leu Val Lys
1               5

<210> SEQ ID NO 48
<211> LENGTH: 7
<212> TYPE: PRT
<213> ORGANISM: Rous sarcoma virus

<400> SEQUENCE: 48

Lys Lys Leu Arg His Glu Lys
1               5

<210> SEQ ID NO 49
<211> LENGTH: 7
<212> TYPE: PRT
<213> ORGANISM: Avian sarcoma virus

<400> SEQUENCE: 49

Lys Lys Leu Arg His Asp Lys
1               5

<210> SEQ ID NO 50
<211> LENGTH: 7
<212> TYPE: PRT
<213> ORGANISM: Homo sapiens

<400> SEQUENCE: 50

Lys Lys Leu Arg His Asp Lys
1               5

<210> SEQ ID NO 51
<211> LENGTH: 7
<212> TYPE: PRT
<213> ORGANISM: Avian sarcoma virus

<400> SEQUENCE: 51
```

```
Lys Lys Leu Arg His Glu Lys
1               5

<210> SEQ ID NO 52
<211> LENGTH: 7
<212> TYPE: PRT
<213> ORGANISM: Homo sapiens

<400> SEQUENCE: 52

Lys Lys Leu Arg His Glu Lys
1               5

<210> SEQ ID NO 53
<211> LENGTH: 8
<212> TYPE: PRT
<213> ORGANISM: Homo sapiens

<400> SEQUENCE: 53

Lys Gln Ala His Glu Leu Ala Lys
1               5

<210> SEQ ID NO 54
<211> LENGTH: 8
<212> TYPE: PRT
<213> ORGANISM: Polyama virus

<400> SEQUENCE: 54

Lys Thr His Arg Phe Ser Lys His
1               5

<210> SEQ ID NO 55
<211> LENGTH: 8
<212> TYPE: PRT
<213> ORGANISM: Sindbis virus

<400> SEQUENCE: 55

Lys Asn Leu His Glu Lys Ile Lys
1               5

<210> SEQ ID NO 56
<211> LENGTH: 9
<212> TYPE: PRT
<213> ORGANISM: Human papilloamavirus type 71

<400> SEQUENCE: 56

Lys His Arg Pro Leu Leu Gln Leu Lys
1               5

<210> SEQ ID NO 57
<211> LENGTH: 7
<212> TYPE: PRT
<213> ORGANISM: Avian encephalomyelitis virus

<400> SEQUENCE: 57

Lys Ser Pro Asn His Val Lys
1               5

<210> SEQ ID NO 58
<211> LENGTH: 8
<212> TYPE: PRT
<213> ORGANISM: Feline sarcoma virus

<400> SEQUENCE: 58

Lys Asn Ile His Leu Glu Lys Lys
1               5
```

```
<210> SEQ ID NO 59
<211> LENGTH: 8
<212> TYPE: PRT
<213> ORGANISM: Homo sapiens

<400> SEQUENCE: 59

Lys Asn Ile His Leu Glu Lys Lys
1               5

<210> SEQ ID NO 60
<211> LENGTH: 10
<212> TYPE: PRT
<213> ORGANISM: Polyoma virus

<400> SEQUENCE: 60

Lys Pro His Leu Ala Gln Ser Leu Glu Lys
1               5                   10

<210> SEQ ID NO 61
<211> LENGTH: 9
<212> TYPE: PRT
<213> ORGANISM: Polyoma virus

<400> SEQUENCE: 61

Lys Gln His Arg Glu Leu Lys Asp Lys
1               5

<210> SEQ ID NO 62
<211> LENGTH: 9
<212> TYPE: PRT
<213> ORGANISM: Polyoma virus

<400> SEQUENCE: 62

Lys Gln His Arg Glu Leu Lys Asp Lys
1               5

<210> SEQ ID NO 63
<211> LENGTH: 12
<212> TYPE: PRT
<213> ORGANISM: Murine leukemia virus

<400> SEQUENCE: 63

Lys Val Pro Val Leu Ile Ser Pro Thr Leu Lys His
1               5                   10

<210> SEQ ID NO 64
<211> LENGTH: 13
<212> TYPE: PRT
<213> ORGANISM: Human T-cell lymphotropic virus type 2

<400> SEQUENCE: 64

Lys Ser Leu Leu Leu Glu Val Asp Lys Asp Ile Ser His
1               5                   10

<210> SEQ ID NO 65
<211> LENGTH: 13
<212> TYPE: PRT
<213> ORGANISM: Homo sapiens

<400> SEQUENCE: 65

Lys Ala Gly Ile Thr Ile Met Val Lys Arg Glu Tyr His
1               5                   10

<210> SEQ ID NO 66
<211> LENGTH: 8
```

```
<212> TYPE: PRT
<213> ORGANISM: Homo sapiens

<400> SEQUENCE: 66

Lys Ser Gly Lys His Leu Gly Lys
1               5

<210> SEQ ID NO 67
<211> LENGTH: 9
<212> TYPE: PRT
<213> ORGANISM: Homo sapiens

<400> SEQUENCE: 67

Lys Arg Arg Glu Gln Leu Lys His Lys
1               5

<210> SEQ ID NO 68
<211> LENGTH: 10
<212> TYPE: PRT
<213> ORGANISM: Homo sapiens

<400> SEQUENCE: 68

Lys Ser Phe Glu Val Ile Lys Val Ile His
1               5                   10

<210> SEQ ID NO 69
<211> LENGTH: 8
<212> TYPE: PRT
<213> ORGANISM: Homo sapiens

<400> SEQUENCE: 69

Lys Lys Lys His Thr Val Lys Lys
1               5

<210> SEQ ID NO 70
<211> LENGTH: 9
<212> TYPE: PRT
<213> ORGANISM: Homo sapiens

<400> SEQUENCE: 70

Lys Ala Gln Lys Asp His Leu Ser Lys
1               5

<210> SEQ ID NO 71
<211> LENGTH: 10
<212> TYPE: PRT
<213> ORGANISM: Homo sapiens

<400> SEQUENCE: 71

His Leu Lys Arg Val Lys Asp Leu Lys Lys
1               5                   10

<210> SEQ ID NO 72
<211> LENGTH: 11
<212> TYPE: PRT
<213> ORGANISM: Homo sapiens

<400> SEQUENCE: 72

Lys Tyr Gly Ser Pro Lys His Arg Leu Ile Lys
1               5                   10

<210> SEQ ID NO 73
<211> LENGTH: 13
<212> TYPE: PRT
<213> ORGANISM: Papilloma virus type 11
```

<400> SEQUENCE: 73

Lys Leu Lys His Ile Leu Gly Lys Ala Arg Phe Ile Lys
1               5                   10

<210> SEQ ID NO 74
<211> LENGTH: 12
<212> TYPE: PRT
<213> ORGANISM: Homo sapiens

<400> SEQUENCE: 74

Lys Gly Asp His Val Lys His Tyr Lys Ile Arg Lys
1               5                   10

<210> SEQ ID NO 75
<211> LENGTH: 13
<212> TYPE: PRT
<213> ORGANISM: Homo sapiens

<400> SEQUENCE: 75

Lys Glu Lys Leu Arg Asp Val Met Val Asp Arg His Lys
1               5                   10

<210> SEQ ID NO 76
<211> LENGTH: 15
<212> TYPE: PRT
<213> ORGANISM: Homo sapiens

<400> SEQUENCE: 76

Lys Leu Gln Ala Arg Gln Gln Gln Leu Leu Lys Lys Ile Glu His
1               5                   10                  15

<210> SEQ ID NO 77
<211> LENGTH: 14
<212> TYPE: PRT
<213> ORGANISM: Homo sapiens

<400> SEQUENCE: 77

Lys Lys Gly Asn Arg Val Ser Pro Thr Met Lys Val Thr His
1               5                   10

<210> SEQ ID NO 78
<211> LENGTH: 9
<212> TYPE: PRT
<213> ORGANISM: Homo sapiens

<400> SEQUENCE: 78

Lys Glu Ile Pro Leu His Phe Arg Lys
1               5

<210> SEQ ID NO 79
<211> LENGTH: 8
<212> TYPE: PRT
<213> ORGANISM: Homo sapiens

<400> SEQUENCE: 79

Lys Lys Lys Pro His Ile Lys Lys
1               5

<210> SEQ ID NO 80
<211> LENGTH: 9
<212> TYPE: PRT
<213> ORGANISM: Homo sapiens

<400> SEQUENCE: 80

Lys Thr Arg His Asp Pro Leu Ala Lys

```
1               5
```

<210> SEQ ID NO 81
<211> LENGTH: 10
<212> TYPE: PRT
<213> ORGANISM: Homo sapiens

<400> SEQUENCE: 81

```
Lys His His Pro Lys Asp Asn Leu Ile Lys
1               5                   10
```

<210> SEQ ID NO 82
<211> LENGTH: 10
<212> TYPE: PRT
<213> ORGANISM: Homo sapiens

<400> SEQUENCE: 82

```
Lys His Lys Arg Lys Lys Phe Arg Gln Lys
1               5                   10
```

<210> SEQ ID NO 83
<211> LENGTH: 10
<212> TYPE: PRT
<213> ORGANISM: Homo sapiens

<400> SEQUENCE: 83

```
Lys Ala Gly Val Ala Phe Leu His Lys Lys
1               5                   10
```

<210> SEQ ID NO 84
<211> LENGTH: 10
<212> TYPE: PRT
<213> ORGANISM: Homo sapiens

<400> SEQUENCE: 84

```
Lys His Lys Arg Lys Lys Phe Arg Gln Lys
1               5                   10
```

<210> SEQ ID NO 85
<211> LENGTH: 10
<212> TYPE: PRT
<213> ORGANISM: Homo sapiens

<400> SEQUENCE: 85

```
Lys Lys Lys Ser Lys Lys His Lys Asp Lys
1               5                   10
```

<210> SEQ ID NO 86
<211> LENGTH: 11
<212> TYPE: PRT
<213> ORGANISM: Homo sapiens

<400> SEQUENCE: 86

```
His Lys Ser Glu Lys Pro Ala Leu Pro Arg Lys
1               5                   10
```

<210> SEQ ID NO 87
<211> LENGTH: 14
<212> TYPE: PRT
<213> ORGANISM: Homo sapiens

<400> SEQUENCE: 87

```
Lys Lys Lys Lys Pro Ser Arg Leu Lys Gly Asp Asn Glu Lys
1               5                   10
```

```
<210> SEQ ID NO 88
<211> LENGTH: 16
<212> TYPE: PRT
<213> ORGANISM: Homo sapiens

<400> SEQUENCE: 88

Lys Thr Lys Lys Gly Asn Arg Val Ser Pro Thr Met Lys Val Thr His
1               5                   10                  15

<210> SEQ ID NO 89
<211> LENGTH: 18
<212> TYPE: PRT
<213> ORGANISM: Homo sapiens

<400> SEQUENCE: 89

Lys His Lys Glu Lys Met Ser Lys Asp Gly Lys Lys Lys Lys Lys Lys
1               5                   10                  15

Ser Lys

<210> SEQ ID NO 90
<211> LENGTH: 9
<212> TYPE: PRT
<213> ORGANISM: Legionella sp.

<400> SEQUENCE: 90

Lys Ile His Leu Ile Ser Val Lys Lys
1               5

<210> SEQ ID NO 91
<211> LENGTH: 9
<212> TYPE: PRT
<213> ORGANISM: Bacillus anthracis

<400> SEQUENCE: 91

His Val Lys Glu Lys Glu Lys Asn Lys
1               5

<210> SEQ ID NO 92
<211> LENGTH: 9
<212> TYPE: PRT
<213> ORGANISM: Bacillus anthracis

<400> SEQUENCE: 92

Lys His Ile Val Lys Ile Glu Val Lys
1               5

<210> SEQ ID NO 93
<211> LENGTH: 15
<212> TYPE: PRT
<213> ORGANISM: Bacillus anthracis

<400> SEQUENCE: 93

Lys Lys Lys Ile Lys Asp Ile Tyr Gly Lys Asp Ala Leu Leu His
1               5                   10                  15

<210> SEQ ID NO 94
<211> LENGTH: 8
<212> TYPE: PRT
<213> ORGANISM: Bacillus anthracis

<400> SEQUENCE: 94

Lys Trp Glu Lys Ile Lys Gln His
1               5

<210> SEQ ID NO 95
```

```
<211> LENGTH: 16
<212> TYPE: PRT
<213> ORGANISM: Bacillus anthracis

<400> SEQUENCE: 95

Lys Lys Leu Gln Ile Pro Ile Glu Pro Lys Asp Asp Ile Ile His
1               5                   10                  15

<210> SEQ ID NO 96
<211> LENGTH: 30
<212> TYPE: PRT
<213> ORGANISM: Bacillus anthracis

<400> SEQUENCE: 96

His Asn Arg Tyr Ala Ser Asn Ile Val Glu Ser Ala Tyr Leu Ile Leu
1               5                   10                  15

Asn Glu Trp Lys Asn Asn Ile Gln Ser Asp Leu Ile Lys Lys
            20                  25                  30

<210> SEQ ID NO 97
<211> LENGTH: 24
<212> TYPE: PRT
<213> ORGANISM: Bacillus anthracis

<400> SEQUENCE: 97

His Ala Val Asp Asp Tyr Ala Gly Tyr Leu Leu Asp Lys Asn Gln Ser
1               5                   10                  15

Asp Leu Val Thr Asn Ser Lys Lys
            20

<210> SEQ ID NO 98
<211> LENGTH: 13
<212> TYPE: PRT
<213> ORGANISM: Bacillus anthracis

<400> SEQUENCE: 98

His Ala Glu Arg Leu Lys Val Gln Lys Asn Ala Pro Lys
1               5                   10

<210> SEQ ID NO 99
<211> LENGTH: 10
<212> TYPE: PRT
<213> ORGANISM: Variola virus

<400> SEQUENCE: 99

Lys His Tyr Asn Asn Ile Thr Trp Tyr Lys
1               5                   10

<210> SEQ ID NO 100
<211> LENGTH: 12
<212> TYPE: PRT
<213> ORGANISM: Variola virus

<400> SEQUENCE: 100

Lys Tyr Ser Gln Thr Gly Lys Glu Leu Ile Ile His
1               5                   10

<210> SEQ ID NO 101
<211> LENGTH: 17
<212> TYPE: PRT
<213> ORGANISM: Variola virus

<400> SEQUENCE: 101

His Tyr Asp Asp Val Arg Ile Lys Asn Asp Ile Val Val Ser Arg Cys
1               5                   10                  15
```

Lys

<210> SEQ ID NO 102
<211> LENGTH: 10
<212> TYPE: PRT
<213> ORGANISM: Variola virus

<400> SEQUENCE: 102

His Arg Phe Lys Leu Ile Leu Asp Ser Lys
1               5                   10

<210> SEQ ID NO 103
<211> LENGTH: 11
<212> TYPE: PRT
<213> ORGANISM: Variola virus

<400> SEQUENCE: 103

Lys Glu Arg Gly His Asn Tyr Tyr Phe Glu Lys
1               5                   10